(12) United States Patent
Chang et al.

(10) Patent No.: US 8,969,007 B2
(45) Date of Patent: Mar. 3, 2015

(54) MICROCHAMBER ELECTROCHEMICAL CELL HAVING A NANOSLOT

(75) Inventors: Hsueh-Chia Chang, Granger, IN (US); Peter Mushenheim, Cuyahoga Falls, OH (US); Sagnik Basuray, Mishawaka, IN (US); Gilad Yossifon, Mazkeret-Batia (IL); Satyajyoti Senapati, Mishawaka, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 157 days.

(21) Appl. No.: 13/508,224

(22) PCT Filed: Nov. 5, 2010

(86) PCT No.: PCT/US2010/055679
§ 371 (c)(1),
(2), (4) Date: Aug. 22, 2012

(87) PCT Pub. No.: WO2011/057107
PCT Pub. Date: May 12, 2011

(65) Prior Publication Data
US 2012/0322076 A1    Dec. 20, 2012

Related U.S. Application Data

(60) Provisional application No. 61/280,638, filed on Nov. 6, 2009.

(51) Int. Cl.
*C12Q 1/68*     (2006.01)
*G01N 27/26*    (2006.01)
*G01N 33/50*    (2006.01)
*G01N 33/487*   (2006.01)

(52) U.S. Cl.
CPC ........ *G01N 33/48721* (2013.01); *C12Q 1/6816* (2013.01); *C12Q 1/686* (2013.01)

USPC ............. 435/6.12; 205/775; 204/403.01; 204/406

(58) Field of Classification Search
CPC ................. G01N 27/02; C12Q 1/686
See application file for complete search history.

(56) References Cited

U.S. PATENT DOCUMENTS

| | | |
|---|---|---|
| 2004/0033515 A1 | 2/2004 | Cao et al. |
| 2006/0073489 A1 | 4/2006 | Li et al. |
| 2006/0191831 A1 | 8/2006 | Hansford et al. |
| 2009/0205960 A1 | 8/2009 | Schaffer et al. |

OTHER PUBLICATIONS

International Preliminary Report on Patentability re PCT/US2010/055679, dated May 8, 2012, 1 pg.
International Search Report and Written Opinion re PCT/US2010/055679, dated Jul. 29, 2011, 6 pgs.
G. Yossifon, Y.-C. Chang and H.-C. Chang, Rectification, Gating Voltage and Interchannel Communication of Nanoslot Arrays Due to Asymmetric Entrance Space Charge Polarization, Phys. Rev. Lett. 103, 154502 (2009), 4 pgs.

*Primary Examiner* — Kenneth R. Horlick
*Assistant Examiner* — David Thomas
(74) *Attorney, Agent, or Firm* — Greenberg Traurig, LLP

(57) ABSTRACT

A microchamber electrochemical cell and method of using the cell for performing quantitative analysis of various charged macromolecules is presented. The microchamber electrochemical cell includes a substrate, opposing electrodes and at least one nanoslot. The substrate is configured to define a pair of opposing fluid reservoirs. The pair of opposing electrodes are respectively positioned within the opposing fluid reservoirs. Each nanoslot is configured to fluidly connect the opposing fluid reservoirs together. The opposing fluid reservoirs of the microchamber electrochemical cell are fluidly connected to each other only through each nanoslot. Each nanoslot is physically restricted to less than 500 nanometers. One method includes the steps of coupling, filling, measuring, obtaining, performing and preparing.

33 Claims, 18 Drawing Sheets

(a)

(b)

MICROCHAMBER ELECTROCHEMICAL CELL HAVING A NANOSLOT

CROSS REFERENCE TO RELATED APPLICATION

This application is a non-provisional application claiming priority from U.S. Provisional Application Ser. No. 61/280,638, filed Nov. 6, 2009, entitled "Nanoslot DNA sensor for quantitative real-time PCR" and incorporated herein by reference in its entirety.

FIELD OF THE DISCLOSURE

The present disclosure relates to measurement devices, in particular to a microchamber electrochemical cell having a nanoslot and a method of using the cell, for use in analyzing various charged macromolecules, such as DNA, by exploiting impedance phenomenon when subjecting AC signals across the nanoslot cell.

BACKGROUND

Being able to quantify in real time the number of charged macromolecules during, for example, a PCR (polymerase chain reaction) amplification will have an enormous impact on genetic sequencing and identification, particularly for field applications where rapidity and portability are essential. Chip-scale PCR can now amplify the number of target DNAs a million fold within 30 minutes. However, detection of amplification and quantification of the number of amplified DNAs (and extrapolation to obtain the original copy number) remains slow or inaccurate. Real-time PCR employing fluorophores and quenchers are fast but suffer by being extremely inaccurate in quantification. They also require delicate and expensive optical detection. Hybridization assays are accurate but time consuming, often requiring more time than the PCR process. Optical detection currently remains the norm for hybridization detection.

Therefore, a need exists for a new and improved macromolecule sensor for. In this respect, the electrochemical cell according to the present disclosure substantially departs from the conventional concepts and designs of the prior art, and in doing so provides an apparatus primarily developed for at least the purpose of providing a convenient means for making it possible to perform Real-Time quantization of PCR DNA samples.

BRIEF DESCRIPTION OF THE DRAWINGS

The disclosure will be better understood and aspects other than those set forth above will become apparent when consideration is given to the following detailed description thereof. Such description makes reference to the annexed drawings wherein.

DETAILED DESCRIPTION

Figure 1:
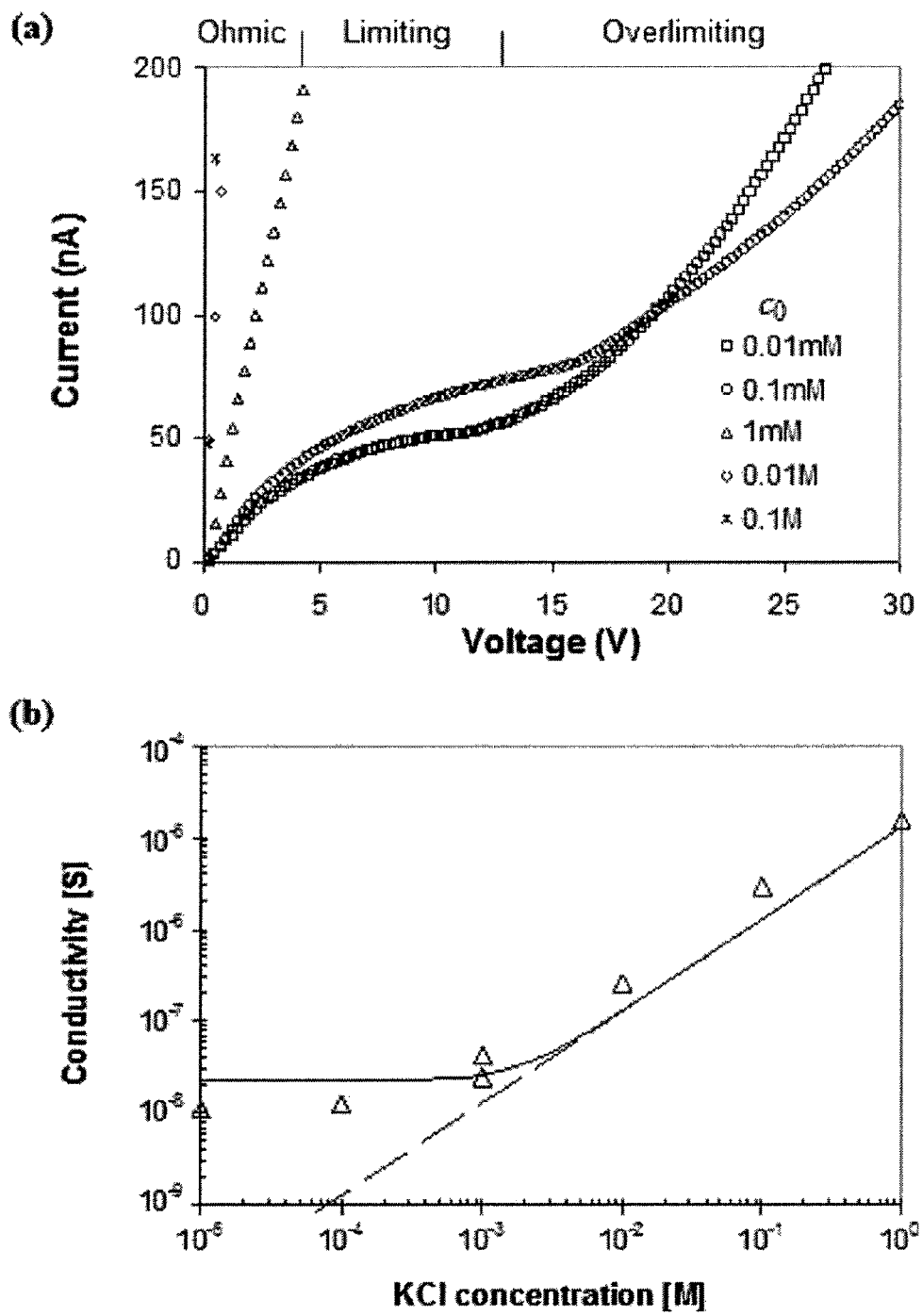
FIGS. 1a-b I-V depicts characteristics and conductance a of nanoslot interface as a function of ionic strengths ($c_o$)

The present disclosure will now be described more fully with reference to the accompanying drawings, in which examples of the disclosure are shown. The disclosure may be, however, embodied in many different forms and should not be construed as being limited to these variations as set forth herein; rather, these examples are provided so that this disclosure will be thorough and complete, and will fully convey the concept of the disclosure to those of ordinary skill in the art.

The drawings are not necessarily to scale and in some instances proportions may have been exaggerated in order to more clearly depict certain features of the disclosure. Further, it should be understood that, although various steps of various the disclosed methods may be shown and described as being in a sequence or temporal order, the steps of any such method are not necessarily limited to being carried out in any particular sequence or order, absent an indication otherwise. That is, the method steps are to be considered to be capable of being carried out in any sequential combination or permutation order while still falling within the scope of the present disclosure.

One I-V characteristic of conducting ion-selective (nanoporous) membranes, such as those in fuel cells, solar cells, mammalian cells with ion channels and desalination devices, is that, at sufficiently high voltages, the current, I, deviates from the usual linear Ohmic dependence on the voltage V. More specifically (see FIG. 1), at some voltage threshold, the differential resistance increases to a large but finite value. Beyond yet another critical "gating"voltage, the differential resistance decreases again to a level that is comparable with that in the Ohmic region. The former part of the I-V curve is referred to as the "limiting resistance" region, while the latter is referred to as the "overlimiting" current region.

The middle high-resistance region is often referred to as the limiting-current region but it is more aptly described as a limiting resistance region with high but finite limiting differential resistance, as the current does not necessary approach a limiting value. The high resistance in this region limits the current density of fuel/solar cells and is a factor in the overall efficiency of these devices. Below the critical voltage of this overlimiting current, the I-V curve assumes initially a linear Ohmic relationship.

Theories suggest that, at high voltages, an extended polarized layer (or, equivalently, space charge layer—SCL) is much thicker than the electric Debye layer (EDL) can appear between the EDL and the electroneutral diffusion layer to sustain the overlimiting current density, which can be much higher than the limiting current density. The collection of these three different regions is termed the concentration polarization layer (CPL). Based on this, an electrokinetic phenomena of the second kind has been postulated to exist.

A straight nanochannel or more accurately nanoslot (because known current standard photolithography techniques cannot produce a width that approaches the submicron length scale of its height) is a simple model (FIG. 2) for an ion-selective nanoporous membrane, as the electric Debye layers (EDLs) of both top and bottom substrates overlap as in a nanopore. Like an ion-selective membrane, the overlapping double layers select the counterions to carry most of the current across the slot. In recent years, fabrication of nanochannels has become possible and the ion transport, ion enrichment, and ion-depletion, rectification of ionic current, limiting, and overlimiting-current phenomena have been examined with these pseudo-ion selective membranes.

While these nonlinear I-V features have been previously studied for pseudohomogenous nanoporous membranes with high pore connectivity and recently for wide nanoslots, the case of a single nanopore (or equivalently, a narrow nanoslot) with three-dimensional field-focusing effects is yet to be scrutinized. Transport issues important at the single nanopore level are mostly neglected (or averaged out) when describing bulk membranes consisting of many nanopores. However, they are expected to become important when the pore separation is sufficiently large such that the interaction among pores does not smooth out the point-sink nature of each pore with respect to field and current flux. As the electromigration ion flux in the electroneutral bulk is controlled by the gradient of the electric potential, which satisfies the Laplace equation in this space charge-free region, the flux density is expected to reflect the equation's classical fundamental solutions with constant, $1/r$ and $1/r^2$ field strengths (r being the radial coordinate) for planar, line, and point sinks. Because these fundamental solutions exhibit extremely different field strengths and length scales, it is quite possible that the different geometries can produce fundamentally different I-V characteristics. Phenomena involving space charge generation and electrohydrodynamics appear to enhanced field focusing which increases the ion flux. Hence, nanoporous membranes with large pore separation and surface heterogeneities may produce a larger overall current even if their void fraction is smaller.

A nonideal permselective membrane or a nanoslot necessitates a model for membranes of finite conductance and a theory that couples all three domains of the problem (i.e., both the CPLs at the anodic and cathodic sides of the membrane, and the nanopore). We employ a simplified model for a non-ideally permselective nanoporous membrane or for a nanoslot, in which the surface charge is included in the averaging of the ion transport and Poisson equations across both solid and liquid phases to produce an effective homogeneous model. The membrane or a nanoslot is assumed to contain fixed charged groups at a uniform volumetric concentration density $\Sigma$. This approach has been previously used for the case of a wide nanoslot, but here it is extended to the axisymmetric nanopore geometry [FIG. 3a-3b] with matching conditions at the entrance to capture the field-focusing effect in the hounding reservoirs (microchambers) that arises from the three-dimensionality of the nanopore. The same field-focusing effect also occurs for true membranes consisting of widely separated nanopores but has yet to be scrutinized.

Figure 3:
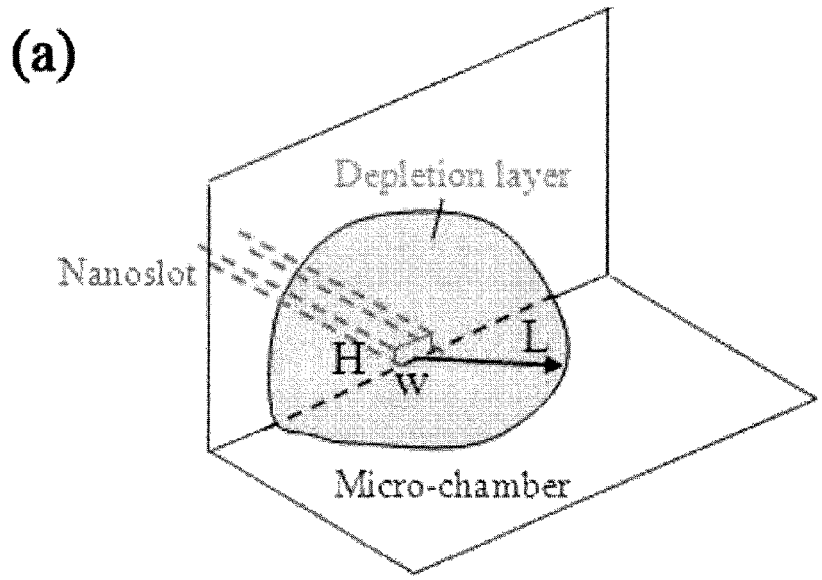
FIGS. 3a-b are schematic depictions of the nanoslot interface and an axisymmetric two-sided micro-nanopore junction.
Figure 3:
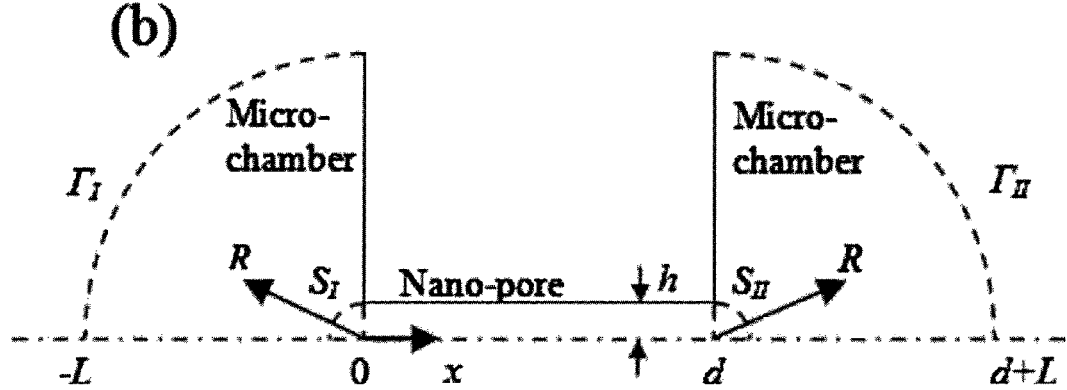

FIG. 3(b) depicts schematically the two-sided axisymmetric micro-nanopore junction problem geometry viewed in profile. We use a spherical coordinate system (R) in the microreservoirs and a Cartesian coordinate system (x) inside the intra-nanopore. The three-dimensional problem can be further simplified into an effective one-dimensional problem, by assuming radial symmetry in the microchamber regions and treating only axial changes within the nanopore region. This assumption is valid because the nanopore radius, h, is much smaller than the dimensions of the microreservoir. In the Ohmic region wherein the nanopore/nanoslot resistance dominates over that of the microreservoirs, it is only the former parameters (i.e., cross-section area, A, length, d, and volumetric fixed charge density $\Sigma$) that control the conductance of the entire system. The parameter $\Sigma$ depends on the nanopore radius h (or nanoslot height, H) and the surface charge density. The latter, unless chemically modified, is usually predetermined by the surface chemistry of the fabrication process. Hence, for the same $\Sigma$, the nanopore [FIG. 3(b)] and nanoslot [FIG. 3(a)] conductance are related to each other by the ratio of the nanopore ($\pi h^2$) to nanoslot (wH) cross-section area. As for microfabricated nanoslot w>>H,h, this ratio is ~$\bar{h}w$<<1.

In the non-Ohmic regions (i.e., limiting-resistance and overlimiting regions) the differential resistance is determined mainly by processes occurring outside the nanochannel/nanopore. A narrow nanoslot of width that is much smaller than the depletion layer length (i.e., w<<L) can be effectively described as a point source/sink in terms of the field-focusing effect as in the case of a nanopore. Hence, for large enough depletion length, the nanoslot and nanopore non-Ohmic differential resistances are again related by the ratio of their cross-section area. It is obvious that a narrow nanoslot (i.e., w≤L) cannot be modeled anymore by the two dimensional approach which is only applicable for wide nanoslots (i.e., w>>L). Instead, the three-dimensional field-focusing effect can be captured by the more simplified axisymmetric nanopore geometry as described in the following.

Both the enrichment region and the depletion region in the two entrances are assigned the CPL length L. By appropriate coordinate transformation (i.e., x=-R at -L<x<-h, and x=d+R at d+h<x<d+L, where L is the CPL length and d is the nanopore length) we can describe all three domains in terms of one axial coordinate x. We chose the following normalization for the axial coordinate $\tilde{x}=Lx$, ionic concentration $\tilde{c}=c_0 c$, electric potential $\tilde{\phi}=(RT/zF)\phi$, ionic flux $\tilde{j}=(Dc_0/L)j$ and electric current density $\tilde{i}=(FzDc_0/L)i$. Here, the tilda stands for dimensional parameters, $c_0$ is the buffer solution concentration, F denotes the Faraday number, z the ion valency, R the universal gas constant, T the absolute temperature, and D the ionic diffusion coefficient. We also define the nondimensional parameter $\delta=\lambda/L$ as the ratio between the EDL length scale, $\lambda=\sqrt{\in_0 \in_f RT/2z^2 F^2 \tilde{c}}$ and the CPL length L. Herein, $\in_0$ is the electric permittivity of vacuum and $\in_f$ denotes the dielectric constant of the electrolyte solution.

As is true for most micro- and nanochannel dimensions and applied voltages, convection effects can be discarded (i.e., negligible Peclet number). A symmetric electrolyte ($z^+=-z^-=z$) of equal diffusivities ($D^+=-D^-=D$) is assumed to simplify the analysis. Thus, $\phi$ and $c^\pm$ satisfy Nernst-Planck equations for the ionic species in the three domains, with radial symmetry invoked in the microreservoirs.

From the concentration polarization layer structure, a clear electroneutral diffusion region with a linear concentration profile is evident beyond the extended polarized layer. This diffusion layer is not necessarily established by tangential electro-osmostic (EO) or convection flow. Instead, it can extend to the electrode or be selected by the vortex instability. The relaxation time of this concentration front in the electroneutral diffusion layer is much longer than that in the polarized layer. As such, the dominant dynamics probed by impedance measurements at frequencies lower than 10 Hz correspond to the dynamics of this electroneutral diffusion front. For a symmetric electrolyte, one can eliminate the electromigration term by adding the cation and anion transport equations to produce a diffusion equation for the ion concentration C. Another equation, corresponding to net charge transport obtained by substracting the anion transport equation from the cation equation, can be coupled to the diffusion equation to replace the two ion transport equations. However, for an electroneutral front, the second charge transport equation is irrelevant and the diffusion equation hence governs the dynamics leading to the linear concentration profile in the diffusion layer. For a constant counterion sink at the interface (mimics the cation perselective influx into the membrane), which was activated at time zero the diffusion front from the from the diffusion equation is governed by $$C(x,t) = C_\infty - \frac{S}{(2\sqrt{D})}\left[2\sqrt{\frac{t}{\pi}} e^{-x^2/(4Dt)} - \frac{x}{\sqrt{D}}\left(1 - erf\left[\frac{x}{2\sqrt{Dt}}\right]\right)\right]$$

wherein the limit of large $x^2/(Dt)$, it simplifies to $$C(x,t) \approx C_\infty - \left(2St^{3/2}\sqrt{D}/x^2\right)e^{-x^2/(4Dt)}.$$

While the diffusive front has a concentration jump that is dependent on the flux S, the location of its front grows as $\sqrt{Dt}$ independent of S. Provided the flux is varied slowly, this self-similar front evolution dynamics stipulates that the thickness of the diffusive front is well described by the simple and universal diffusive scaling $\sqrt{Dt}$, independent of the frequency and the instantaneous electric field.

Figure 4:
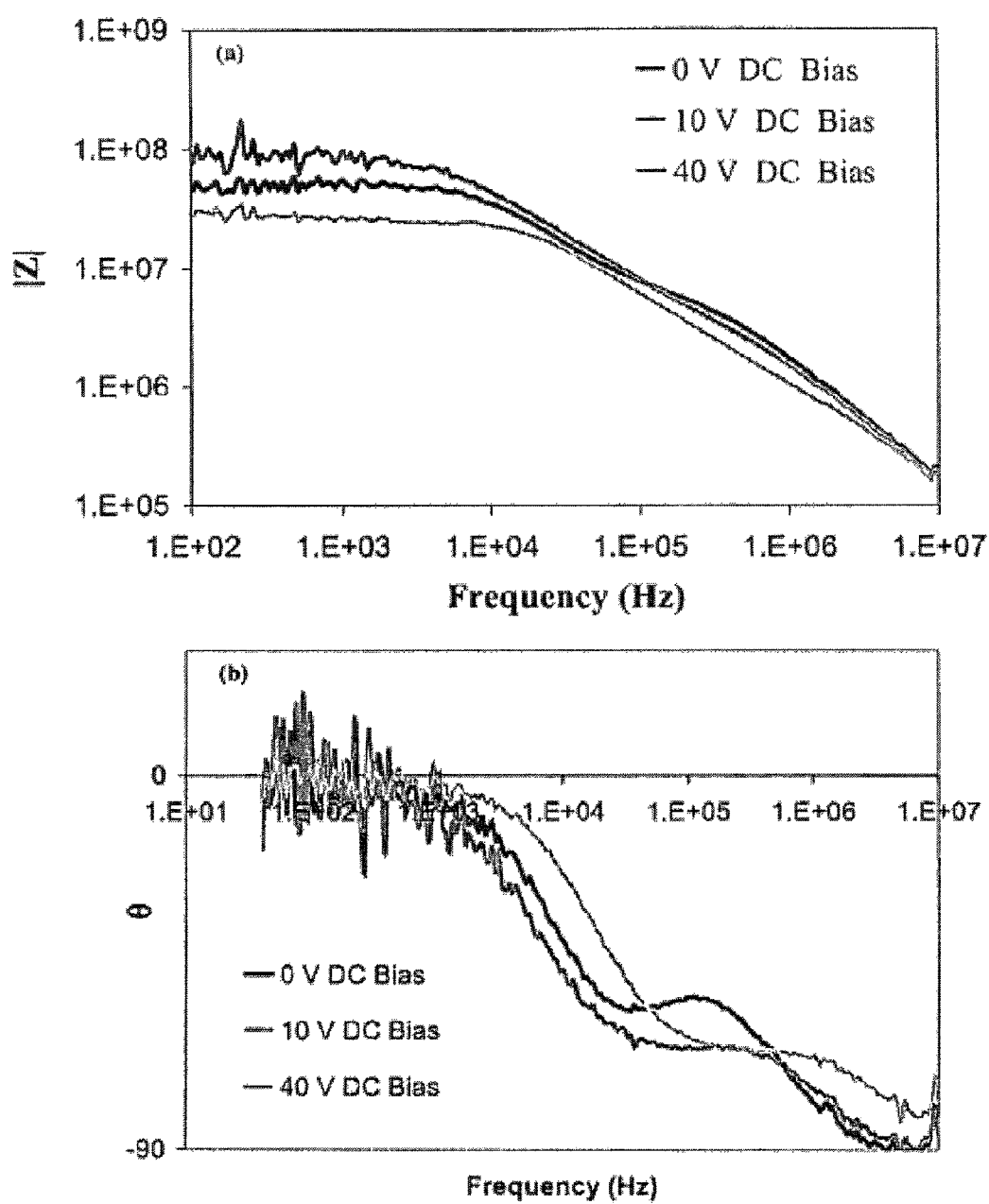
FIGS. 4a-b are magnitude and phase of the AC impedance across the nanoslot interface with different DC biases at an electrolytic strength of 0.1 mM.

This diffusive dynamics also occurs at high frequency and low voltages when there is very little polarization—when the period is much shorter than the charging time of the polarized layer at this low voltage. After Fourier transform, the concentration C assumes the form $$C(x,\omega) \approx C_\infty + (C_0 - C_\infty)e^{-x\sqrt{i\omega/D}},$$

where $C_0$ is the concentration at the nanochannel-electrolyte interface. If there is very little electromigration, then the current at the surface (x=0) is entirely diffusive and the inverse impedance assumes the characteristic Warburg form with real and imaginary parts of the same amplitude at all frequencies, $$\frac{1}{Z} = \frac{FA}{V}z\sqrt{D}(C_0 - C_\infty)\sqrt{i\omega} = \frac{FA}{V}z\sqrt{D}(C_0 - C_\infty)\sqrt{\omega/2}(1+i),$$

where A is the cross-section area of the nanoslot. This Warburg impedance is observed across many electrodes and its 45° phase is also observed in FIG. 4 at intermediate frequencies due to counterion diffusion fronts from the nanoslit.

Here we present the first direct experimental proof for instability by using an applied AC electric field to form the depletion layer intermittently at alternating ends of a linear nanoslot. A one-dimension theory is adequate because the instability occurs with the depletion layer, which is at least 10 times smaller than the radius of curvature of the entrance. The length of the slot and the microreservoir dimension [inset in FIG. 2(c)]. The field does vary somewhat at different locations along the entrance and leads to the slightly varying vortex size in FIG. 5(a), but there is very little lateral communication with the depletion layer. Moreover, due to flow continuity, the depth-averaged flow rate in the microchannel, where the depletion layer resides, must be equal to that in the nanoslot with a minute cross section area. Consequently, the average velocity in the depletion layer is extremely small, and EO convective contribution to the instability is negligible. As the DL is much thicker than the SCL, the formation dynamics of the depletion layer is dominated by the former. Quite fortuitously, the DL grows in a universal manner that allows us to precisely determine when vortices arrest this universal front evolution and select the CPL thickness. For symmetric electrolytes with negligible ion accumulation at the thin SCL, the DL is a diffusive front (that propagates into the Ohmic bulk solution) with a nearly constant flux S (positive when directed into the membrane surface), and the classical solution in a semi-infinite domain is $$C(x,t) = C_\infty - \frac{S}{(2\sqrt{D})}\left[2\sqrt{\frac{t}{\pi}} e^{-x^2/(4Dt)} - \frac{x}{\sqrt{D}}\left(1 - erf\left[\frac{x}{2\sqrt{Dt}}\right]\right)\right],$$

wherein the limit of large $x^2/(Dt)$, it simplifies to $$C(x,t) \approx C_\infty - \left(2St^{3/2}\sqrt{D}/x^2\right)e^{-x^2/(4Dt)}/x^2.$$

While the diffusive front has a concentration jump that is dependent on the flux S, the location of its front grows as $\sqrt{Dt}$ independent of S. Provided the flux is varied slowly, this self-similar front evolution dynamics stipulates that the thickness of the diffusive front is well described by the simple and universal diffusive scaling $\sqrt{Dt}$, independent of the frequency and the instantaneous electric field.

We exploit this field-independent universality of the depletion layer dynamics by using an AC (square-wave or sine-wave) field to sustain depletion layers of different thickness dynamically. Arrest of the growth of this DL by the instability would then be represented by a break from this universal dynamics. By using a low frequency (<10 Hz), we should then be able to produce a depletion layer thickness $\sqrt{Dt}$ larger than 10 μm. Such a large thickness allows us to carry out fluorescent imaging of the depletion layer and to verify the vortex instability. As earlier instabilities theories predict a particular scaling of the vortex pair wavelength to the depletion layer thickness, our images would allow us to verify the occurrence of the instability. There is no external stirring in our microdevice, and this mechanism for selecting the diffusion layer thickness is ruled out immediately. As our junction is nearly planar and perpendicular to the applied electric field, we do not expect an EO vortex of the second kind to develop. Any significant EO flow would disrupt the diffusive scaling.

In one example, a chip containing the micro/nanochannel junction was fabricated using standard photolithography technologies and consists of two large holes connected by a single nanoslot of 200 nm in depth and about 1 mm in length, d, at its center [inset in FIG. 5(c)]. Reservoirs were used on top of the holes wherein platinum electrodes (0.3 mm in diameter) were introduced. The two holes were drilled through a 1 mm thick Pyrex (Corning 7740) glass slide. The nanoslot was patterned on the other slide and etched through the α-Si layer. These two glass slides were then anodically bonded. In order to visualize the polarized regions, we used either rhodamine dye molecules of fluorescently tagged human serum proteins in combination with confocal microscopy. All of the data and imaging are collected for phosphate buffered saline buffer and fluorescent molecules concentrations of 30 and 10 μM, respectively. This corresponds to a Debye length of about 55 nm, which assures a strong EDL overlap inside the nanoslot resulting in its cation permselectivity.

FIG. 5(a), depicts the maximum extent of the enrichment and depletion layers at different frequencies in the rang 0.01-1 Hz. For frequencies higher than 1 Hz, the extent of the CPL is almost not discernible. As expected due to its diffusive formation nature, the extent of the CPL is insensitive to whether it is in the enrichment or depletion phase. The most peculiar observation in FIG. 5(a) is the pattern formation in the depletion layer, while no such pattern exists in the enrichment phase. This is in agreement with the theory because an unstable SCL does not exist in the enrichment layer; hence, no instability can occur. FIG. 5(b) is a blowup of one such depletion region revealing its inner structure, which consists of a vortex pair with streaks that resemble the streamlines from the simulations of other workers. It is also clear from the images that the vortex size decrease with the increase of the frequency (corresponds to the decrease of the CPL extent) while their number increase accordingly. FIG. 5(c) depicts the maximum attainable depletion length versus different field frequencies. Also depicted is the simple $\sqrt{Dt}$ scaling of the CPL extent, wherein a reasonable value of $D \sim 4.7 \times 10^{-5}$ m$^2$/s was chosen for the diffusion coefficient. Although vortices are observed within the evolving diffusion layer during this self-similar interval, they appear not to affect the diffusion layer growth. On the other hand, a clear break of this self-similar growth is observed beyond t=10 s (0.01 Hz), corresponding to a critical diffusion layer thickness of 220 μm, and is associated with the fully established vortices that are responsible for the growth arrest. The arrest of the depletion layer also results in the arrest of the enrichment layer [cf. FIG. 5(a)]. The arrested CPL is still thin compared to the slot width, and hence boundary conditions should not contribute to the arrest of its growth.

Figure 6:
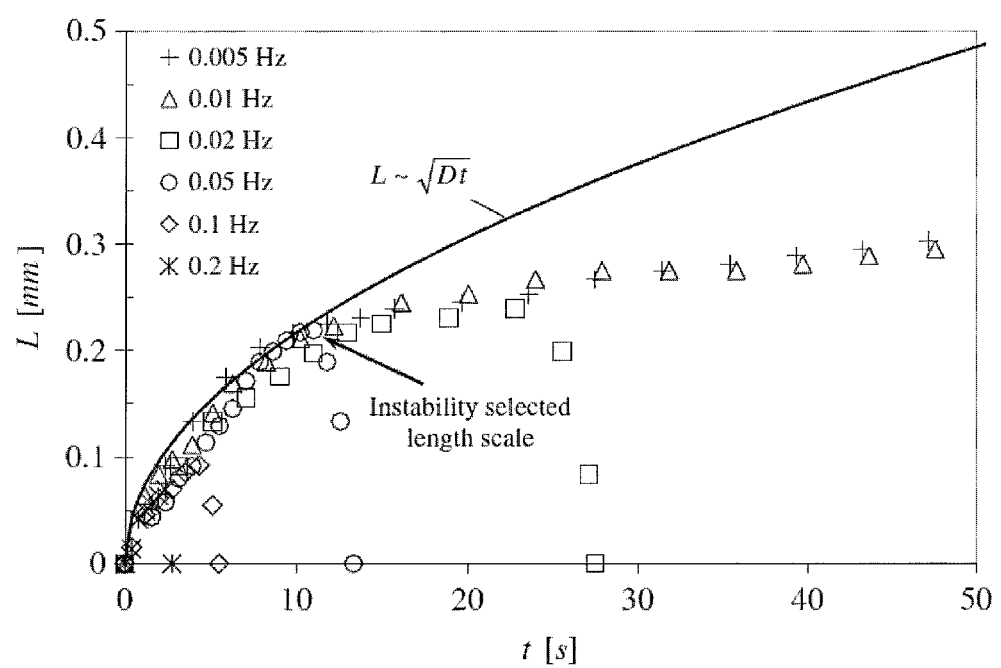
FIG. 6 time evolution of the instantaneous depletion layer (L) at different AC frequencies.

FIG. 6 depicts the instantaneous depletion layer (CPL) thickness for different frequencies. The higher-frequency values and the presaturated values for the low-frequency experiments collapse and obey the simple $\sqrt{Dt}$ scaling, suggesting that the universal diffusive formation dynamics is observed. That the self-similar diffusive scaling captures the front evolution dynamics supports the fact that convection is suppressed in our nanoslot device. A slight upward drift in the depletion layer thickness persists after the departure from the self-similar growth but at a much smaller rate than the diffusion scaling, before falling when the polarity changes. The slow drift is most likely because the small tangential ion migration due to the slight transverse curvature of the vortex array.

Figure 7:
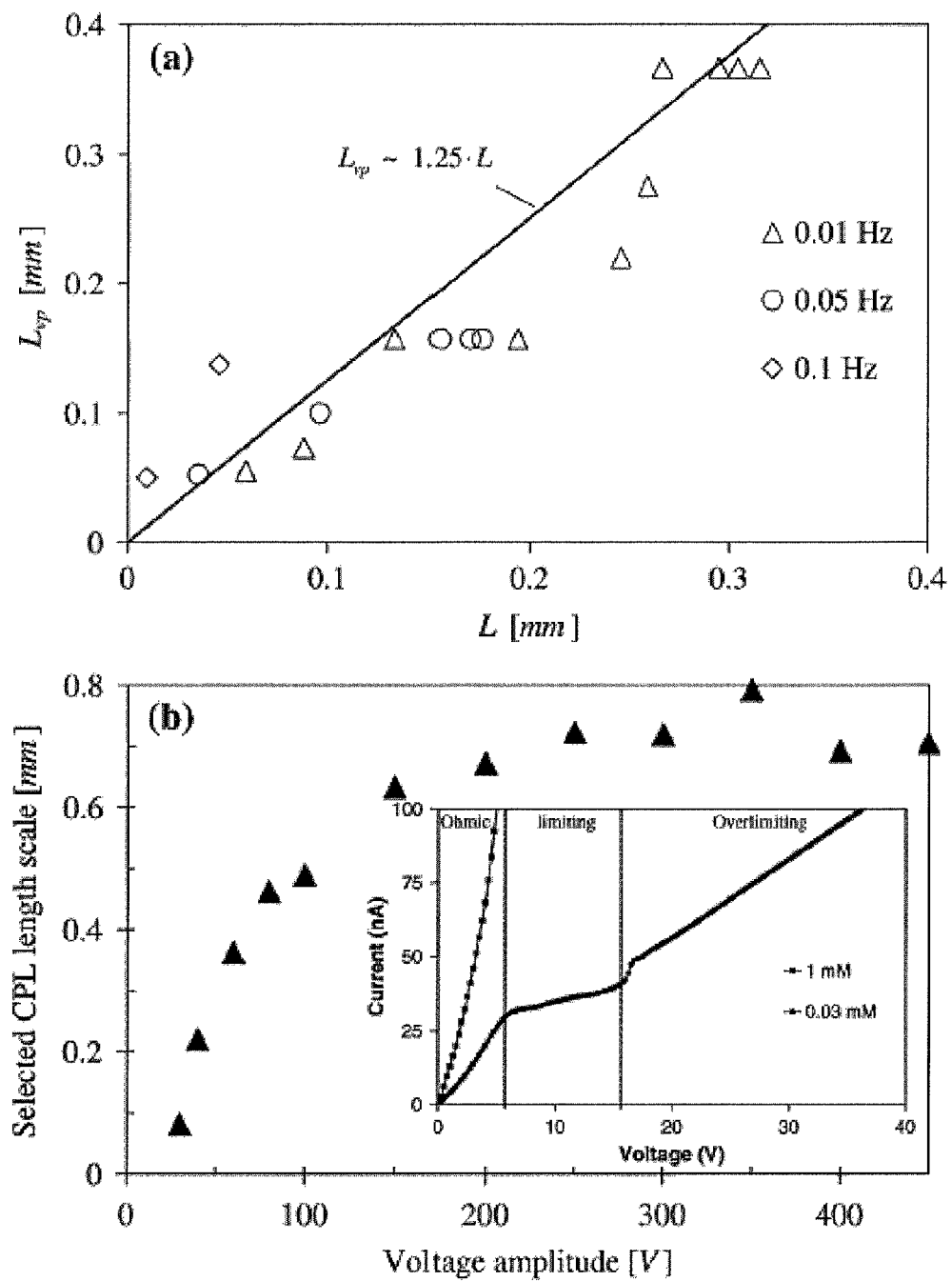
FIGS. 7a-b depict width of the periodicity cell Lvp versus the instantaneous depletion layer (L) at different AC frequencies and depicting CPL length as a function of AC amplitude.

FIG. 6 indicates that the CPL thickness is selected by the instability. The cross-plot of the imaged diffusion layer thickness against the vortex pair wavelength in FIG. 7(a) clearly shows that it obeys the linear scaling predicted by others with an empirical coefficient of 1.25, another confirmation that it is the same instability (the complex process of wave length selection by small vortices breaks up through fusion and transformation into still larger vortices until a quasisteadylike pattern is formed as seen by others.

Figure 5:
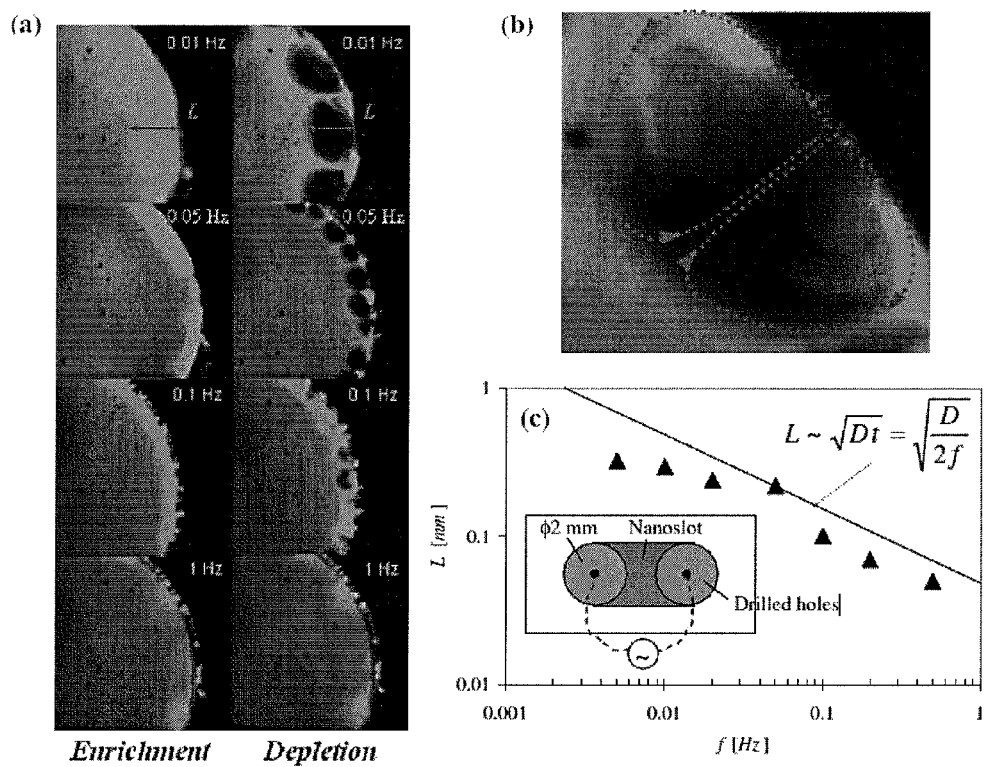
FIG. 5a-c are confocal image snapshots of the maximum CPL extent of instantaneous depletion layer (L) and a Log-Log graph of the measured L at different AC frequencies.

Although the self-similar $\sqrt{Dt}$ dynamics is independent of voltage and frequency, the selected depletion layer thickness, represented by its value when it deviates from the self-similar $\sqrt{Dt}$ scaling (as indicated in FIG. 5), is independent of frequency but dependent on voltage, as shown in FIG. 6(b). The voltage dependence is inconsistent with the predictions that predict that the depletion layer thickness should decrease as 1/E with the respect to the field E, as it is assumed to be the convection-diffusion boundary layer generated by external stirring due to induced EO flow of the 2nd kind and hence scales as the $-\frac{1}{2}$ power of the flow, which is quadratic in E. This contradiction again suggests that the observed vortices are not due to natural EO flow or EO flow induced by the SCL but rather by the instability of the SCL. The saturation at high voltages most likely occurred because the CPL is now comparable in dimension to the nanoslot width, such that the curved front is no longer pseudo-one-dimensional. The measured I-V curve of the nanoslot shown in the inset in FIG. 7(b) indeed exhibits an overlimiting current regime beyond 20 V, in agreement with the observed onset voltage for the instability in the same figure, which it selects a CPL thickness.

Figure 2:
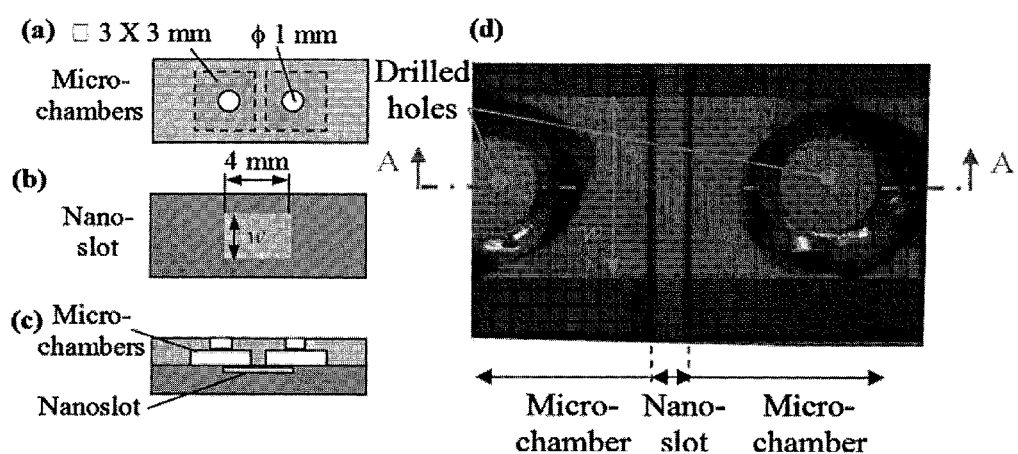
FIGS. 2a-d are various views of the nanoslot microchamber electrochemical cell.

Nanoslots of different widths were fabricated to connect between two microchambers. The fabrication technique is similar to the anodic bonding procedure. Briefly, nanoslots 0.5 mm long but of different widths 2.5 mm, 1 mm, 0.5 mm, and 50 μm were patterned on a 190 nm thick polysilicon layer deposited on a 1 mm thick Pyrex glass (Corning 7740) substrate (FIG. 2) using standard photolithography techniques. A reactive $CF_4/O_2$ plasma then etched into the polysilicon layer at a rate of 100 nm/min. The depth of the resulting channel was determined by the thickness of the polysilicon layer (i.e., H=190 nm) as was verified using an α-stepper profilometer. The microchambers 3×3 mm$^2$ were patterned on a second 1 mm thick Pyrex glass slide on which masking layers of Cr/Au (30/300 nm) were deposited. After developing through the mask layers, the microchambers were wet-etched using 52% HF solution for a predetermined time to achieve a depth of about 50 μm. Two entrance holes 1 mm in diameter were then drilled in the center of each microchamber and the rest of the masking layers were etched away using a Cr- and Au-etchants (FIG. 2a). After cleaning in HNO₃ solution for about 10 min, the two slides were bonded together (FIGS. 2c and 2d). To ensure good bonding, the wafers were preheated for 2 h at 400° C. and bonded at the same temperature at 1000 V for 1 h. Reservoirs made of flexible silicon were used on top of the openings wherein platinum electrodes were introduced. The nanoslot was filled by introducing distilled, deionized (18 MΩ cm) water into the large fluidic reservoirs and allowing capillary forces to draw the water across the nanoslot. The electrical voltage source and I-V converter (Agilent Technologies, 4155 B Semiconductor Parameter Analyzer) were connected to the fluidic channel with negligible resistive loss via platinum wires inserted into the reservoirs. The channels were cleaned of ionic contaminants using electrophoretic pumping. The ionic current was observed to decay while 10 V were applied across the channels to drive out ionic impurities. The reservoirs were periodically flushed with fresh solution until the current equilibrated to a minimum, which typically took ~20 min. This procedure was also followed by displacing different dilutions of a 1 M potassium chloride (KCl) solution to change the ionic strength and control the degree of EDL overlap.

In order to prepare the microchamber electrochemical cells for testing, the nanoslots were cleaned of ionic contaminants using electrophoretic pumping under the application of 10V across the slots. The reservoirs were periodically flushed with fresh solution until the current equilibrated to a minimum, which typically took ~20 min.

The electrochemical impedance spectra data presented in the Nyquist plots were obtained by connecting the Platinum electrodes to a potentiostat (Gamry PCI4/300 Potentiostat/ Galvanostat/ZRA). After removing the cleaning DI water from the system and replacing it with the solution to be tested, an AC field of a constant amplitude 50 mV rims was applied across the nanoslot while the frequency was logarithmically swept from 300 kHz to 60 mHz. Upon completion, (which took approximately 5.25 m) the same sweep would be performed again multiple times in order to capture the time dependence of the system's signature impedance signal.

The real time PCR samples were run using an ordinary PCR and a nano-slot in combination. The initial PCR broth of 50 ul (0.5 ul TAQ Polymerase, 2 ul Ecoli solution in TAE 1× Buffer, 5 ul 10× TaQ Buffer, 4 ul Primers, the redt DI water) had a conductivity of 3.2 mS/cm. We further looked at the conductivity post PCR operations and it was still the same at 3.2 mS/cm. The slot was initially filled with DI water and the I/V characteristics was studied in details to see whether the fabrication of the slot was done precisely. Post measurement once the slot worked, we measured the impedance spectrum of the nano-slot filled with DI water and called it our control base line from where all the relative shifts were measured. After the PCR was run, a different slot was used. This is to avoid cross-contamination by using the same slot for both PRE and POST PCR operations. The same baseline was created using DI water. Each slot is now emptied of 30 ul of DI water from each micro-reservoir and 20 ul of pre-PCR broth and post-PCR broth was added. The relative shift from the DI water base line was measured and quantified for different cycles of PCR.

To obtain the measured I-V curves in FIG. 1, the applied voltage was stepped in 0.25 V increments every 3 s, during which time current transients were observed to decay completely. In the low concentration limit, the three distinct I-V regimes for the wide nanoslot are indeed observed: a linear Ohmic region, followed by a limiting-resistance region with a small slope (large limiting differential resistance) and finally an overlimiting region [(FIG. 1(a)]. These data are in qualitative agreement with previous experimentally obtained I-V curves for true nanoporous membranes and also for nanochannels.

At high enough concentrations >10⁻³ M, only the Ohmic region is observed [FIG. 1(a)], irrespective of the nanoslot width. The thinner Debye length stipulates that EDLs do not overlap within the slot and the nanochannel's perm-selectivity, space charge, and superior conductivity are lost—it is no longer a model for an ion-selective nanoporous membrane. Note that the conductance at the low-voltage Ohmic region does not scale linearly with the ionic strength at its low values (FIG. 1b), suggesting that intraslot resistance is relevant. Ohmic resistance is hence not just due to external resistance, as is assumed in earlier theories involving an infinitely conducting membrane. The conductivity within the slot is finite and must be considered to quantitatively capture the true I-V characteristics.

Figure 8:
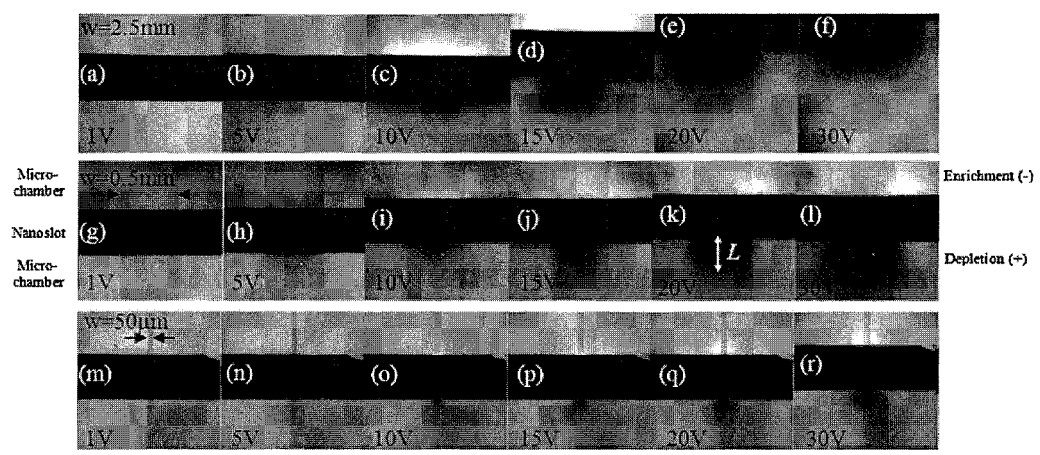
FIGS. 8a-r are confocal image snapshots of quasisteady depletion enrichment layers as a function of different widths of the nanoslot interface.
Figure 9:
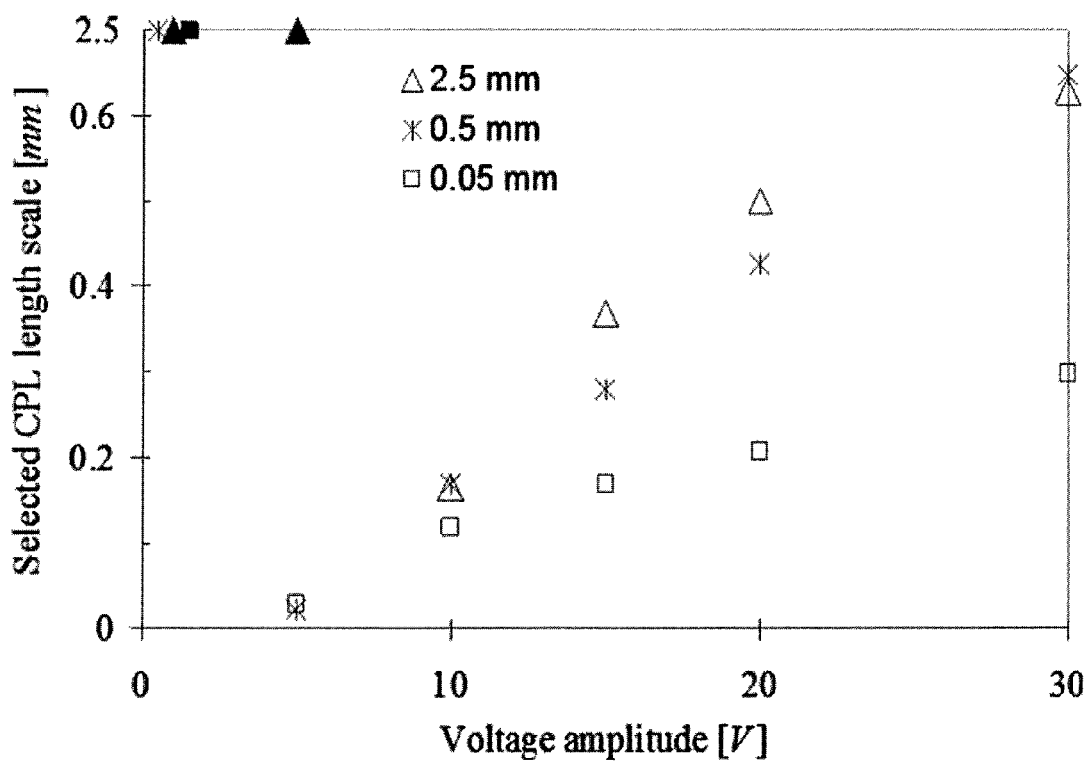
FIG. 9 depicts CPL length as a function of AC amplitude for different widths of the nanoslot interface.
Figure 10:
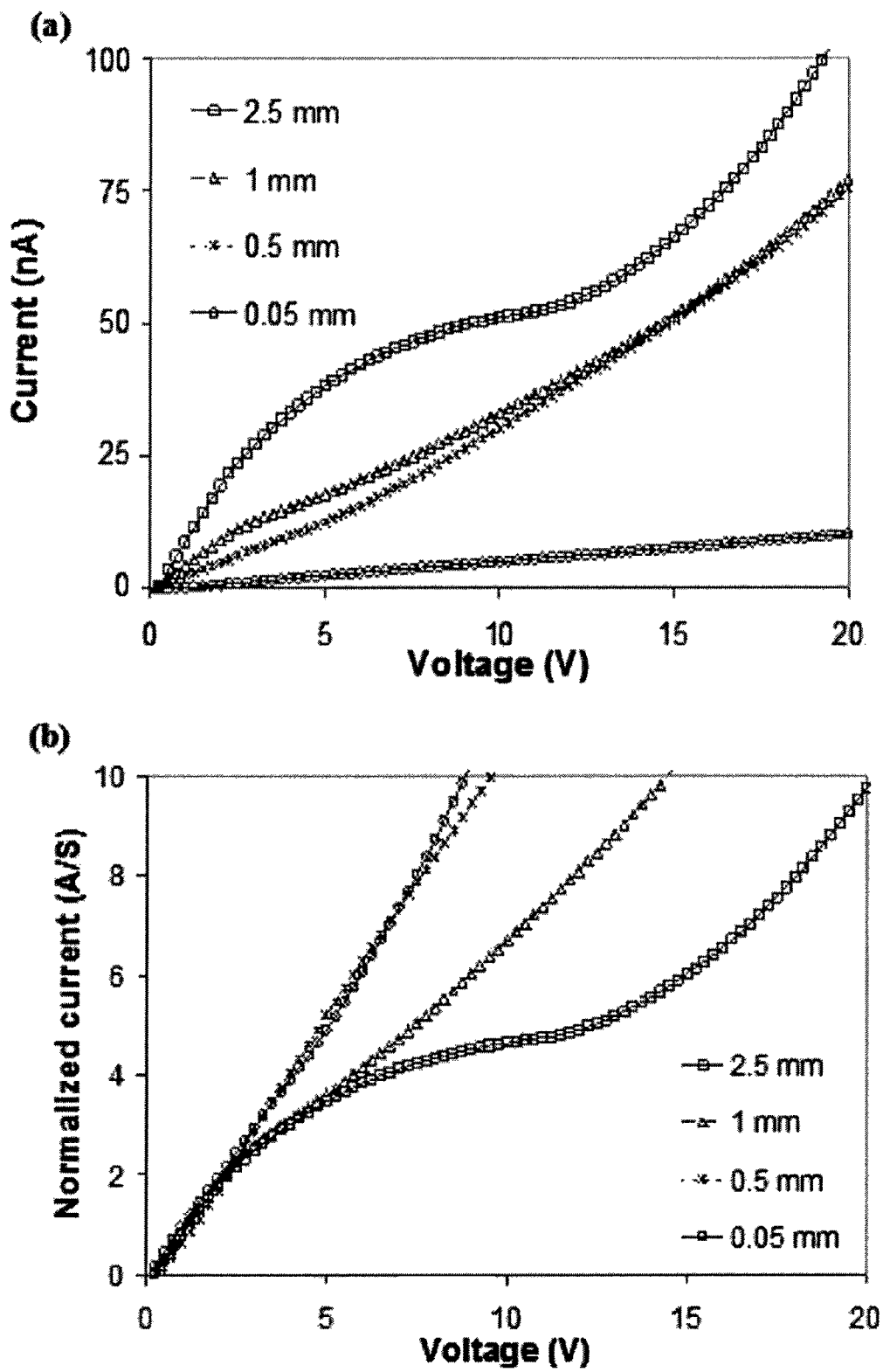
FIG. 10a-b are I-V characteristics and normalized conductivity as a function of AC amplitude for different widths of the nanoslot interface.
Figure 11:
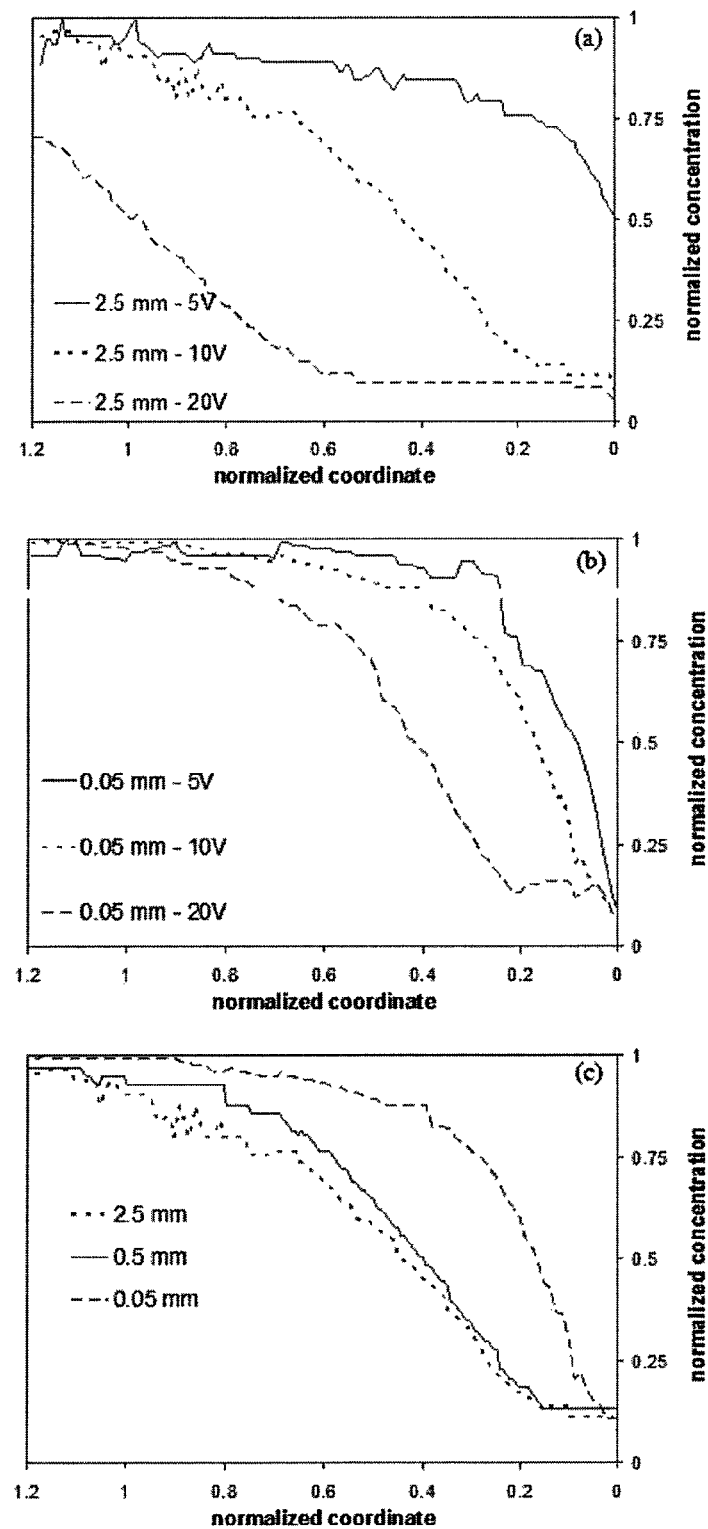
FIG. 11 are normalized concentration profile of the depletion layer at the anodic side as a function of applied voltage for different widths of the nanoslot interface.

In order to visualize the polarized regions, we used positive-charged Rhodamine dye molecules (counterions of the nanoslot) at 10 μM concentration. When a large enough electric field, beyond the critical voltage for the limiting-resistance region, is applied across the nanoslot, an enrichment region at the cathodic entrance of the nanoslot is observed with high dye concentration while a depletion region is observed at the anodic side where the dye enters the nanoslot, as seen in FIG. 8 for the nanoslots of different width. Instead of a periodic array of depletion regions observed on the anodic side of the wide nanoslot, a single and significantly smaller depletion region is obtained for the narrow nanoslot [FIGS. 8(n)-8(r)]. This is also confirmed by plotting the selected depletion layer length (defined as L in FIG. 8), which approximates the selected CPL length scale, for nanoslots of different widths at different applied voltages (FIG. 9). At voltages below ~5 V for narrow and ~10 V for wide nanoslots (FIG. 8), it was hard to discern any depletion and the CPL length scales (see also FIG. 8). It was hence assumed that the CPL extends all the way to the electrodes (~2.5 mm), as indicated by the filled symbols in FIG. 9. The critical voltage in FIG. 9, when the observed CPL length undergoes a discontinuous drop, is in agreement with the onset voltage of the overlimiting region in FIG. 10. Beyond this critical voltage, the depletion is clearly discernable at the anodic side of the nanoslot interface and became more pronounced with voltage. The CPL length increased with voltage until it reached again the slot-electrode separation. However, compared to conditions below the overlimiting region, the concentration gradient in the CPL is much higher and increases with decreasing slot width. That the ionic concentration gradients in the depletion layer of the narrower nanoslot are more severe is clearly seen in FIG. 11(c), which compares the concentration profiles of different slots at 10 V. FIGS. 11(a) and 11(b) depict the voltage dependence of the concentration profile on the applied voltage for the wide (2.5 mm) and narrow (50 μm) nanoslots, respectively. It clearly shows the increase of the total CPL length scale in FIG. 9 and also the emergence of the polarized layer (SCL), with a flattened concentration profile inside the high-gradient depletion region, at higher voltages. These concentration plots were extracted from the fluorescent intensity profile across the depletion region at the anodic side of the nanoslot.

Figure 12:
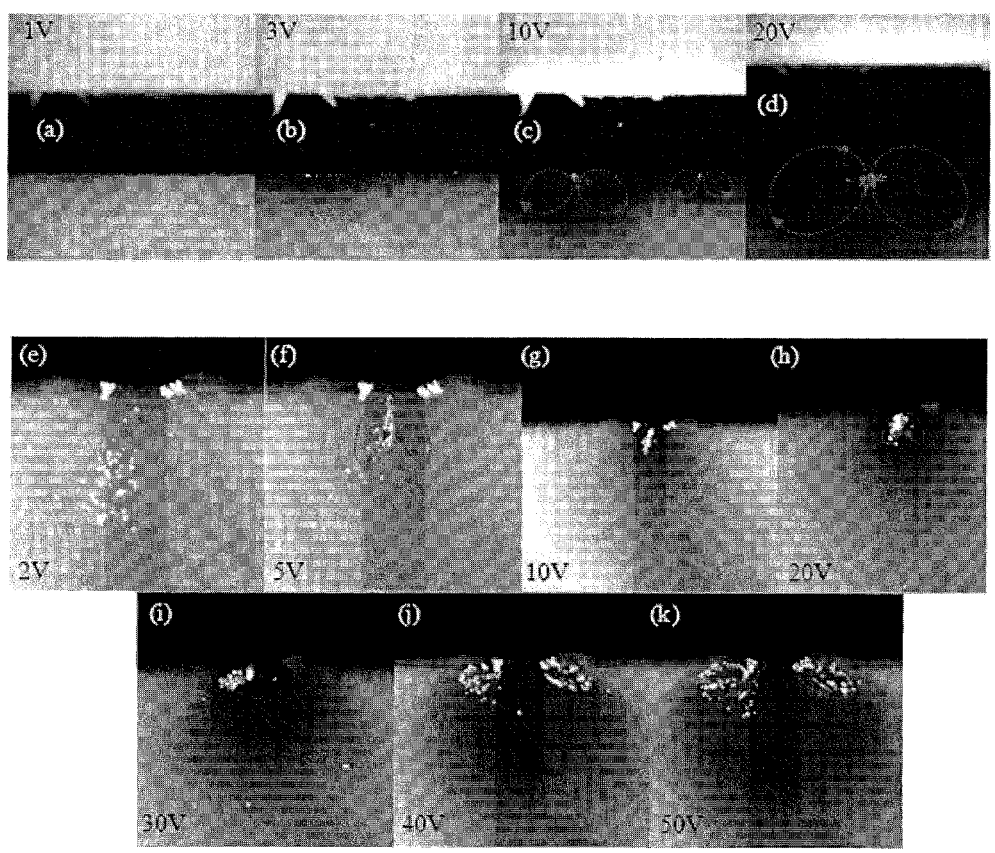
FIG. 12a-k are confocal image snapshots of the quasisteady depletion layer for different widths of the nanoslot interface in the presence of Rhodamine dye molecules.
Figure 13:
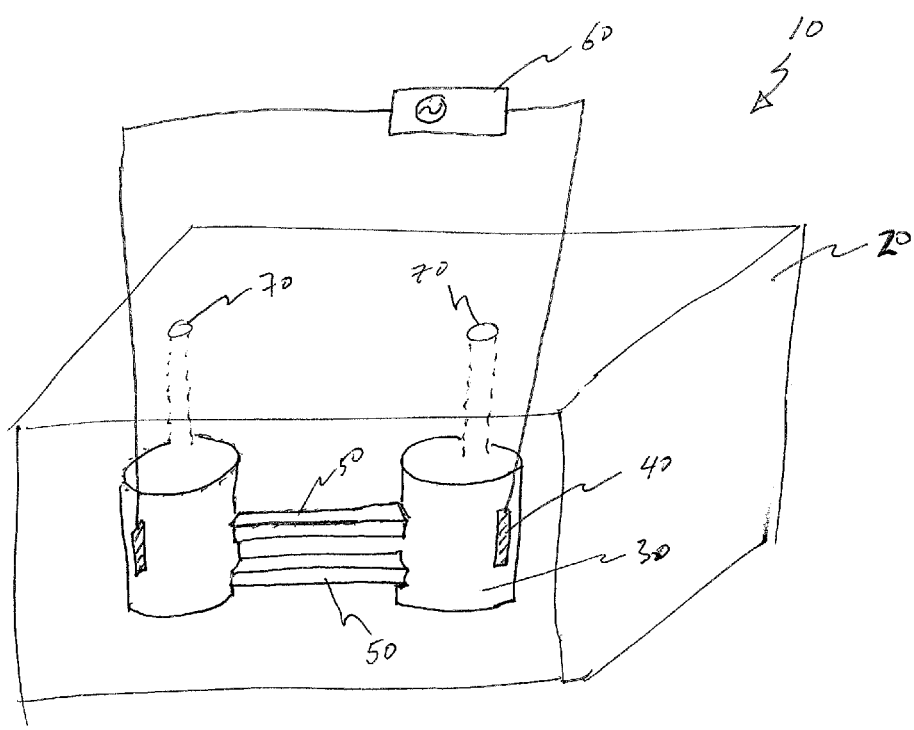
FIG. 13 is a perspective transparent view of another embodiment of the nanoslot microchamber electrochemical cell.

In order to visualize, in a qualitative manner, the inner flow structure of these depletion regions, we used fluorescent polymer microbeads (Duke Technologies) of 1.2 μm in size and 0.02% volumetric concentration, reminiscent of the micro-particle imaging velocimetry (μ-PIV) technique used for quantitative determination of the velocity field. In the case of a wide nanoslot [FIGS. 12(a)-12(d), an array of depletion regions appear, with each region encompassing a single vortex pair (see the schematic vortex streamlines in FIG. 12(c). Individual vortex pairs in the array appear at different locations along the nanoslot entrance. The bright spots in FIGS. 12(b)-12(d) are the stagnation points of the different vortex pairs where colloids tend to accumulate. They eventually synchronize and coalesce in a complex manner to create a single (thicker) depletion layer and a single (larger) vortex pair at large enough voltages [see the transition from FIGS. 12(c) and 12(d)]. In contrast, the depletion side of the narrow nanoslot always produces a single vortex pair [FIGS. 12(e)-12(k)] at the nano-microchannel junction corners (see the schematic vortex streamlines). Because the colloids mirror the background flow, they follow the closed-streamline patterns of the vortex pair and tend to accumulate there. Hence, the accumulation of colloids, as seen also in the stills pictures of FIG. 12, is an indication of the existence of a vortex there. Interestingly, an elevated voltage does not only increase the size of the depletion region, and its associated vortex pair, but also tilts the vortex pair toward the horizontal plane consisting of the nanoslot entrance [compare the schematic vortex streamlines of FIGS. 12(h) and 12(k)]. Furthermore, the vortex pair appears at the narrower slots before the emergence of the depletion layer [see FIGS. 12(e) and 12(f)]. This suggests that the single vortex pair of the narrow slots originates from a mechanism different from the initial vortex array in the wider slots. The latter is most likely due to the SCL instability but the dominant corner effects of the former suggests that corner polarization (e.g., ICEO) at low voltages and space charge emergence concurrent with large tangential electric field component (due to the field-focusing geometry) at higher voltages (>10 V) are responsible for the vortex pair generation of narrow slots. This vortex pair enhances the ionic current through the nanoslot [as seen in FIG. 10(b)], as its mixing action reduces the selected CPL length scale.

For a sufficiently large depletion layer length relative to the nanoslot width, the three-dimensional field-focusing results in an almost spherically shaped depletion layer. More precisely, for the fabricated narrow nanoslot [FIG. 3(a)], it is a quarter of a sphere as the bottom surface of the chip behaves as a symmetry plane. This observation allows us to produce a simple model that connects the narrow nanoslot to the nanopore. Both share the same field-focusing behavior, but with different radial geometries, and the quarter-sphere depleted region of the nanoslot is exactly one half of the half-sphere region in front of the nanopore [FIG. 3(b)].

We find the thickness of the depletion layer at one entrance to be comparable to that in the enrichment region in the other. However, due to the low ionic strength in the depletion layer, it is quite obvious that it is the depletion layer that controls the current and the thickness of both layers. The vortices and the resulting constrained depletion layer only appear beyond a critical voltage of about 10 V [FIGS. 12(c) and 9] and 5 V [FIGS. 12(e) and 9] for the wide and narrow nanoslots, respectively. Below this voltage, the CPL extends to the electrode and beyond it the vortex pair selects a smaller CPL dimension that increases monotonically with voltage, as shown in FIGS. 9 and 12.

Referring now to the drawings, and in particular FIGS. 13 to 18 thereof, examples of the present disclosure are shown and discussed. One example of the microchamber electrochemical cell 10 comprises a substrate 20, a pair of opposing electrodes 40, and at least one nanoslot 50. The substrate 20 is configured to define a pair of opposing fluid reservoirs 30. The pair of opposing electrodes 40 is positioned in the opposing fluid reservoirs 30. Each nanoslot 50 is configured to fluidly connect together the opposing fluid reservoirs 30 when the opposing fluid reservoirs 30 are flooded such that the opposing fluid reservoirs 30 are fluidly connected to each other only through each nanoslot 50. In this example, each nanoslot 50 is physical restricted to less than 500 nanometers.

The microchamber electrochemical cell 10 may also comprise a plurality of nanoslots 50 fluidly connect together the opposing fluid reservoirs 30 when the opposing fluid reservoirs 30 are flooded such that the opposing fluid reservoirs 30 are fluidly connected to each other only through each of the nanoslots 50.

In one example of the microchamber electrochemical cell 10, each nanoslot 50 is physically restricted to about 200 nanometers. Another example is that each nanoslot 50 is physically restricted to at least 50 nanometers. The particular geometric shape design of each nanoslot 50 can be any known shape so long as each nanoslot 50 is physical restricted to less than 500 nanometers. One example configuration of the nanoslot 50 is that it is shaped as a flattened tunnel having a width, a height and a length in which the height of the nanoslot 50 is physically restricted and the width and length may be any size. Another example shape of each nanoslot 50 is that it is shaped as a square tunnel shape having an equal width and height in which the height and width are physically restricted to less than 500 nanometers. Yet another example shape of each nanoslot 50 is that it is shaped as a cylindrical tunnel shape having a diameter and a length in which the diameter is physically restricted to less than 500 nanometers. Still yet another example shape of each nanoslot 50 is that it is shaped as an tapered hourglass tunnel shape having a narrow waist diameter and a length in which the narrow waist diameter is physically restricted to less than 500 nanometers.

It is believed that by lowering the height of the nanoslot 50 the sensitivity of the microchamber electrochemical cell 10 increases. That is a smaller restriction in each nanoslot 50 results in concentrating the electric field generated at the electrodes through the nanoslot 50 physical restrictions. It is believed that an increase in the electric field affects the ion transport through each nanoslot 50 and effectively increases the depletion layer. As a result, the larger depletion layer allows charged molecules more distant from the electrodes to affect the change in measured impedances. However, a practical physical size limitation is to be expected. In particular, it appears that nanoslots 50 of about 25 nanometers or less result in unacceptably high impedance measurements in the gigaohm range. As a result, it is our understanding that nanoslots 50 with these extremely diminutive restriction dimensions of about 25 nanometers or less effectively restrict ion transport between the opposing fluid reservoirs 30 and consequently prevent effective formation of a depletion layer which results in preventing any measurable change in conductivity from being detected.

An feature of the example nanoslot 50 is that its surfaces can be constructed in such a way that a surface charge resides on theses surfaces. We believe that this surface charge, which can be either positive or negative, can be native to the material, formed during processing of the material, or controlled by a separate technique known in the surface modification fabrication arts. It is believed that this surface charge allows the transport of counter-ions and effectively prevents or inhibits co-ions from entering the nanoslots 50.

The compositional makeup of the material used to construct each nanoslot 50 may be made from any known material and may be made of the same or different material makeup as that or the substrate 20. Some examples of materials envisioned to define each nanoslot 50 are those selected from the group consisting of quartz, silica, silicon, polypropylene, polyethylene, polyethylene terephthalate, polyurethanes, polyacryls, polymethacryls, epoxy polymers, polystyrenes, polysiloxanes, and admixtures thereof.

The microchamber electrochemical cell 10 may also comprise an impedance measuring device 60 coupled to the opposing electrodes 40. It is envisioned that any commercially available impedance measuring device 60 can be incorporated. One example of the impedance measuring device 60 is that it is configured to impose an AC sinusoidal electromagnetic perturbation at a single set frequency between 10 MHz to 0.01 Hz with an AC amplitude between 1 mV to 10 V and configured to measure a resultant impedance modulus across the opposing electrodes 40 through each nanoslot 50. Another example of the impedance measuring device 60 is that it is configured to provide AC sinusoidal frequency perturbations swept between 10 MHz to 0.01 Hz having an AC amplitude of between 1 mV to 10 V and configured to measure real and imaginary components of a resultant impedance spectrum measured across the opposing electrodes 40 through each nanoslot 50. Yet another example of the impedance measuring device 60 is that it is also configured to impose a DC voltage across the opposing electrodes 40.

The microchamber electrochemical cell 10 may also comprise a pair of opposing inlet/outlet ports 70 through the substrate 20 which are configured to be in fluid communications with the opposing reservoirs.

The compositional makeup of the opposing electrodes 40 may be any known commercially available material such as those selected from the group consisting of aluminum, carbon, chromium, cobalt, germanium, gold, graphite, graphene, iridium, molybdenum, osmium, palladium, platinum, ruthenium, rhodium, silicon, tantalum, titanium, titanium nitride, tungsten, tungsten nitride, vanadium, vitreous carbon, and mixtures thereof.

The compositional makeup of the substrate 20 may be any known commercially available material such as those selected from the group consisting of quartz, silica, silicon, polypropylene, polyethylene, polyethylene terephthalate, polyurethanes, polyacryls, polymethacryls, epoxy polymers, polystyrenes, polysiloxanes, polyethyleneterephthalate, polystyrene, and admixtures thereof.

The total volume of the opposing fluid reservoirs 30 may be any volumetric displacement. One example is that the total volume of the opposing fluid reservoirs 30 is configured to be between about 50 to 5000 microliters.

One method example comprises using the microchamber electrochemical cell 10 as part of a real-time PCR (Polymerase Chain Reaction) quantitative method which comprises the steps of preparing, obtaining, filling, performing, coupling, and measuring. It is understood that the steps of any of these disclosed methods can be performed in any sequence and are not limited to the sequential order presented herein. It is also understood that the some of the claimed method steps may also be performed simultaneously to each other.

The preparing step comprises preparing a PCR assay cocktail comprising a target template, complementary primers, a buffer, a salt, a polymerase enzyme, and NTP (nucleotide triphosphate) monomers.

The obtaining step comprises obtaining a microchamber electrochemical cell 10 comprising: a substrate 20 defining a pair of opposing fluid reservoirs 30; a pair of opposing electrodes 40 in the opposing fluid reservoirs 30; and at least one nanoslot 50 fluidly connecting together the opposing fluid reservoirs 30 such that the opposing fluid reservoirs 30 are fluidly connected to each other only through each nanoslot 50 in which each nanoslot 50 is physical restricted to less than 500 nanometers; and an impedance measuring device 60.

The filling step comprises filling the opposing fluid reservoirs 30 of the microchamber electrochemical cell 10 with the PCR assay cocktail such that both opposing fluid reservoirs 30 are in fluid communications with each other through each nanoslot 50.

The performing step comprises performing several PCR cycles in which each PCR cycle comprises a denaturation step, an annealing step and an elongation step to produce amplicons of the target template.

The coupling step comprises coupling the opposing electrodes 40 to the impedance measuring device 60.

The PCR assay mixture can be comprise any compositional makeup as long as it comprises a target template, complementary primers, a buffer, a salt, a polymerase enzyme, and NTP (nucleotide triphosphate) monomers. As such the NTP monomers of the PCR assay mixture may comprise deoxynucleotide triphosphates (dNTP) monomers or ribosenucleotide triphosphate (rNTP) monomers. The complementary primers of the PCR assay mixture may comprise sense and antisense primers. The target template of the PCR assay mixture may comprise a DNA target template or an RNA target template. The polymerase enzyme of the PCR assay mixture may comprise Taq polymerase. The salt of the PCR assay mixture may comprise magnesium divalent cations and potassium cations.

Another method example comprises using the microchamber electrochemical cell 10 to perform quantitative analysis of a macromolecule. This method comprises the steps of making, getting, flooding, connecting and detecting.

The making step comprises making an assay mixture containing the macromolecule.

The getting step comprises getting a microchamber electrochemical cell 10 comprising: a substrate 20 defining a pair of opposing fluid reservoirs 30; a pair of opposing electrodes 40 in the opposing fluid reservoirs 30; and at least one nanoslot 50 fluidly connecting together the opposing fluid reservoirs 30 such that the opposing fluid reservoirs 30 are fluidly connected to each other only through each nanoslot 50 in which each nanoslot 50 is physical restricted to less than 500 nanometers; and an impedance measuring device 60.

The flooding step comprises flooding the opposing fluid reservoirs 30 of the microchamber electrochemical cell 10 with the assay mixture such that both opposing fluid reservoirs 30 are in fluid communications with each other.

The connecting step comprises connecting the opposing electrodes 40 to the impedance measuring device 60.

The detecting step comprises detecting an AC impedance between the opposing electrodes 40 through each nanoslot 50 while providing an AC sinusoidal electromagnetic perturbation at a frequency between 10 MHz to 0.01 Hz with an AC amplitude between 1 mV to 10 V.

The measuring or detecting steps may comprise measuring an AC impedance across the opposing electrodes 40 while providing an AC sinusoidal electromagnetic perturbation at a frequency between 10 MHz to 0.01 Hz with an AC amplitude between 1 mV to 10 V.

The methods may also further comprise the step of correlating the AC impedance measured across the pair of opposing electrodes 40 with a molar concentration of the amplicons.

The AC impedance may be measured or detected at any temperature in which it example that the AC impedance is measured or detected at room temperature of about 20° C.

The AC sinusoidal electromagnetic perturbation may be at a single frequency or be swept at a broad frequency range. One example imposition of the AC sinusoidal electromagnetic perturbation is that it is at a single frequency of about 10

Hz. Another example imposition of the AC sinusoidal electromagnetic perturbation is that it is swept at a frequency between about 1 MHz to 0.1 Hz and that the AC impedance measured or detected is an impedance spectrum.

The measured AC impedance may be any AC impedance such as the real component of the AC impedance (Z'), the imaginary component of the AC impedance (Z"), the modulus of the AC impedance (Z).

Referring now to FIG. 1 which depicts a perspective view of a variation of the microchamber electrochemical cell 10 of the disclosure. The microchamber electrochemical cell 10 shown having the substrate 20 defining a pair of opposing fluid reservoirs 30. The pair of opposing electrodes 40 is shown respectively positioned in the opposing fluid reservoirs 30. Each nanoslot 50 is shown configured to provide fluid connects between the opposing fluid reservoirs 30 when the opposing fluid reservoirs 30 are flooded with a solvent. The impedance measuring device 60 is also shown coupled to the opposing electrodes 40 for measuring the AC impedance across the opposing chambers through the two nanoslots 50. The inlet/outlet ports 70 are also shown traversing through the substrate 20 and into the opposing chambers of the microchamber electrochemical cell 10 for providing a route of introducing fluid assay samples into each of the opposing chambers.

Figure 14:
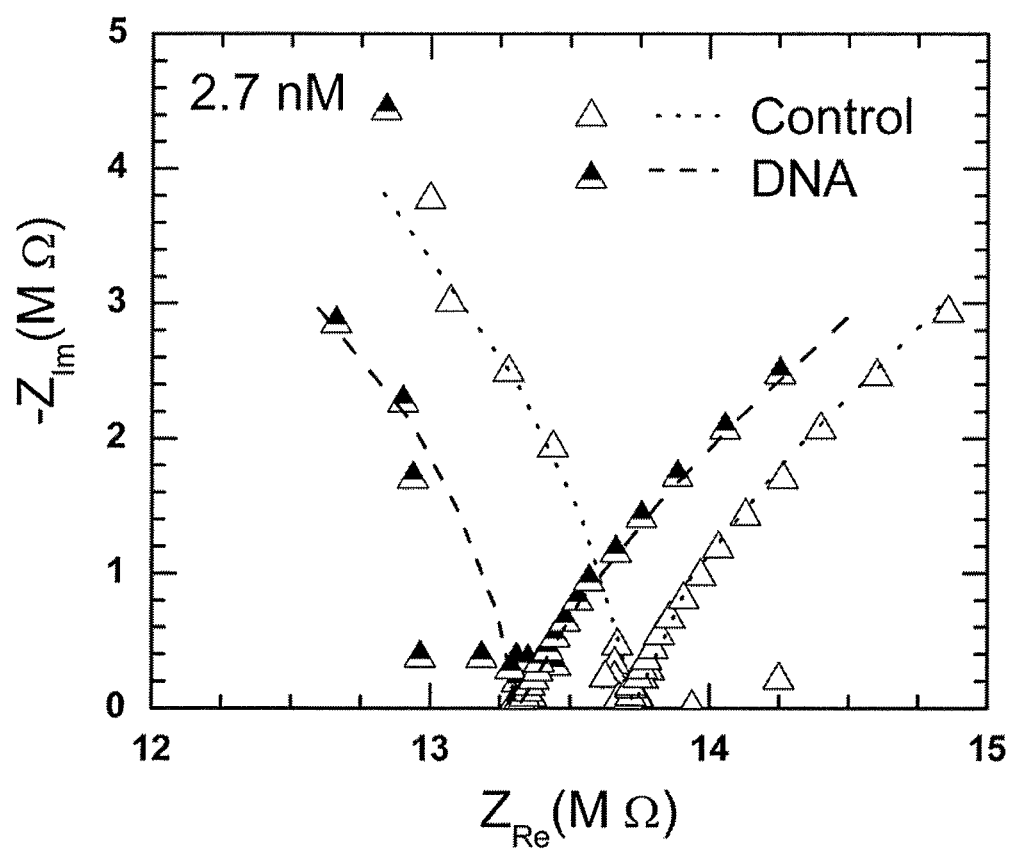
FIG. 14 depicts resultant impedance spectra (i.e., Nyquist plots) measured across the opposing electrodes of the nanoslot microchamber electrochemical cell flooded with either a control sample or with a sample containing 2.7 nM of DNA.
Figure 15:
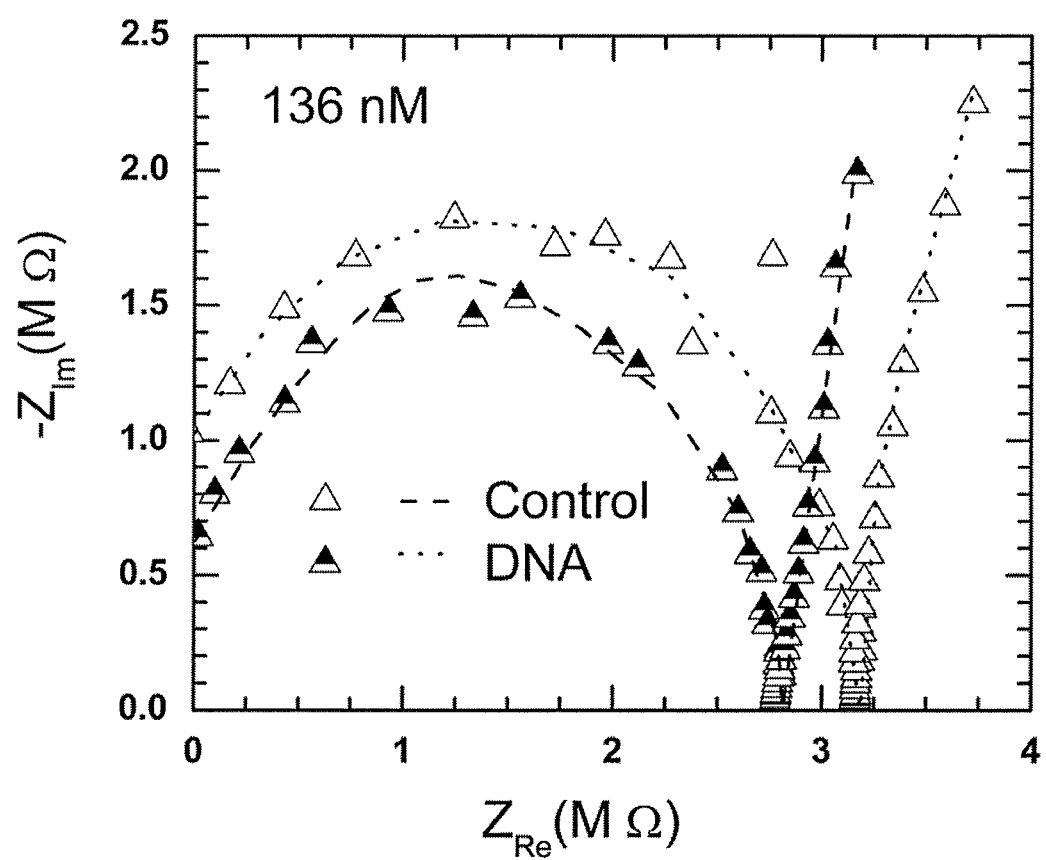
FIG. 15 depicts resultant impedance spectra (i.e., Nyquist plots) measured across the opposing electrodes of the nanoslot microchamber electrochemical cell flooded with either a control sample or with a sample containing 136 nM of DNA.

FIGS. 14-15 depict resultant impedance spectra (i.e., Nyquist plots) measured by the impedance measuring device 60 of the microchamber electrochemical cell 10. In each figure, the impedance spectra are shown corresponding to a control sample having essentially no amplicon DNA. FIG. 14 also depicts another impedance spectrum corresponds to a PCR assay mixture containing approximately 2.7 nM of DNA. FIG. 15 also depicts another impedance spectrum that corresponds to the PCR assay mixture containing approximately 136 nM of DNA.

FIG. 15 depicts a bar diagram showing percent change in Zreal (i.e., Z') of the DNA samples with respect to their corresponding measured Zreal of their respective control samples.

Figure 16:
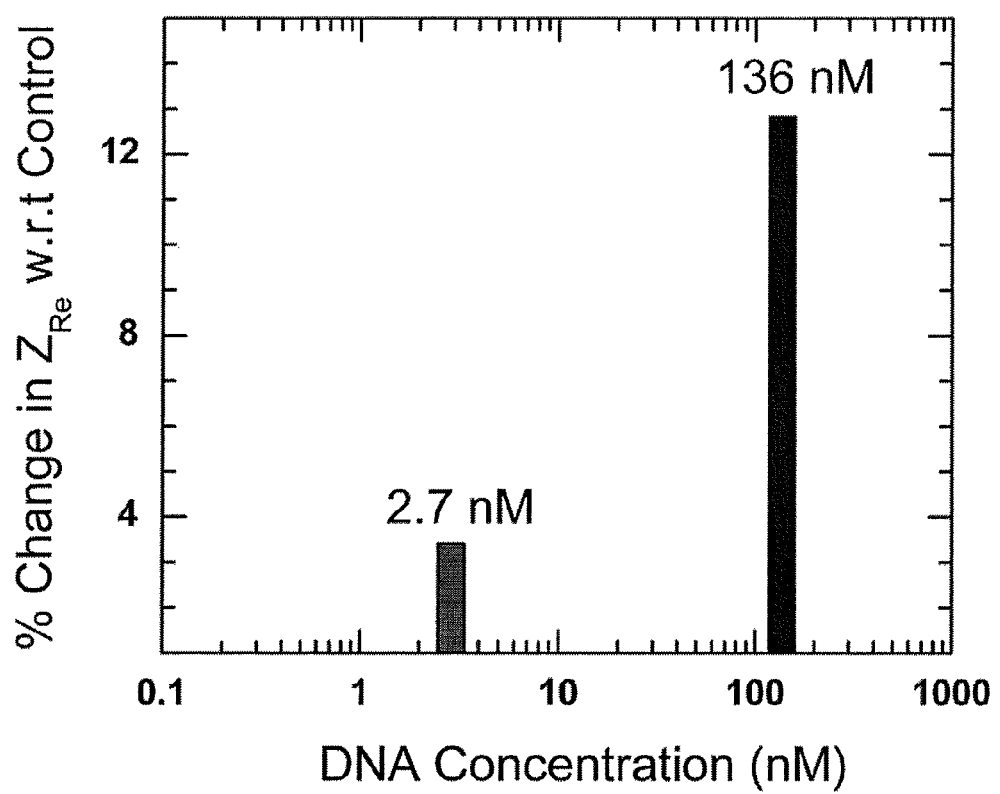
FIG. 16 depicts a bar diagram showing percent change in Zreal (i.e., Z') of the DNA samples with respect to their respective control samples.
Figure 17:
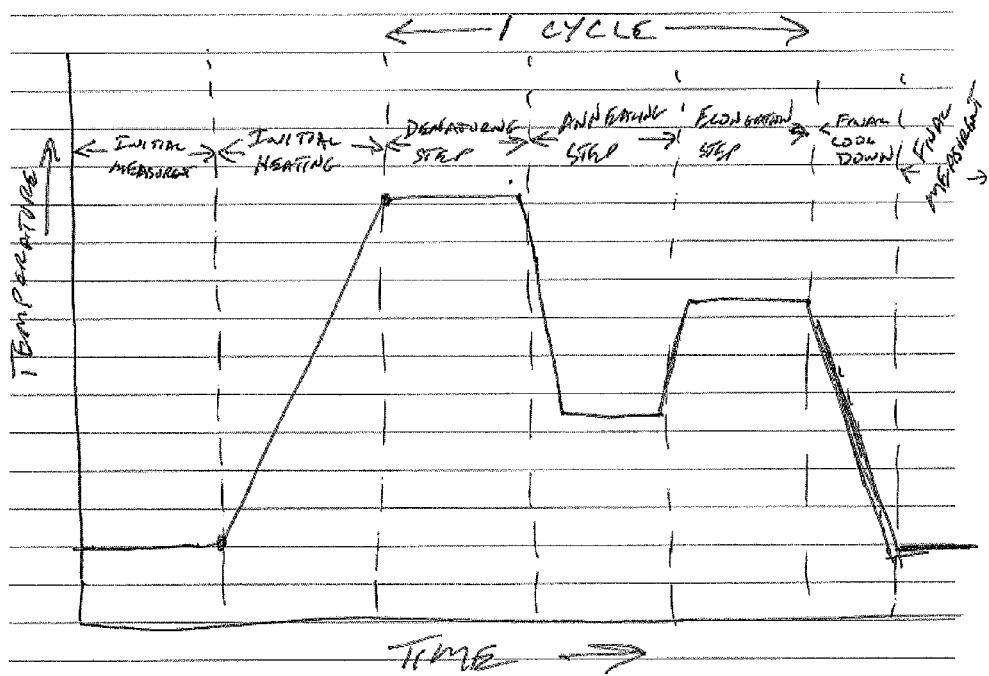
FIG. 17 depicts a stylized temperature profile as a function of time in performing the PCR amplification operations using the nanoslot microchamber electrochemical cell.

FIG. 16 depicts a stylized temperature profile as a function of time in proceeding in a PCR operation using the microchamber electrochemical cell 10. Although the initial impedance measurement across the opposing electrodes 40 40 is preferably performed at room temperature, the measurement may be performed at any temperature and at any time. It is preferable that the initial and final measurement temperatures are the same. It is noted that any number of PCR cycles may be performed between the initial and final measurements. Each PCR cycle preferably comprises the steps of denaturing, annealing and elongation steps.

Figure 18:
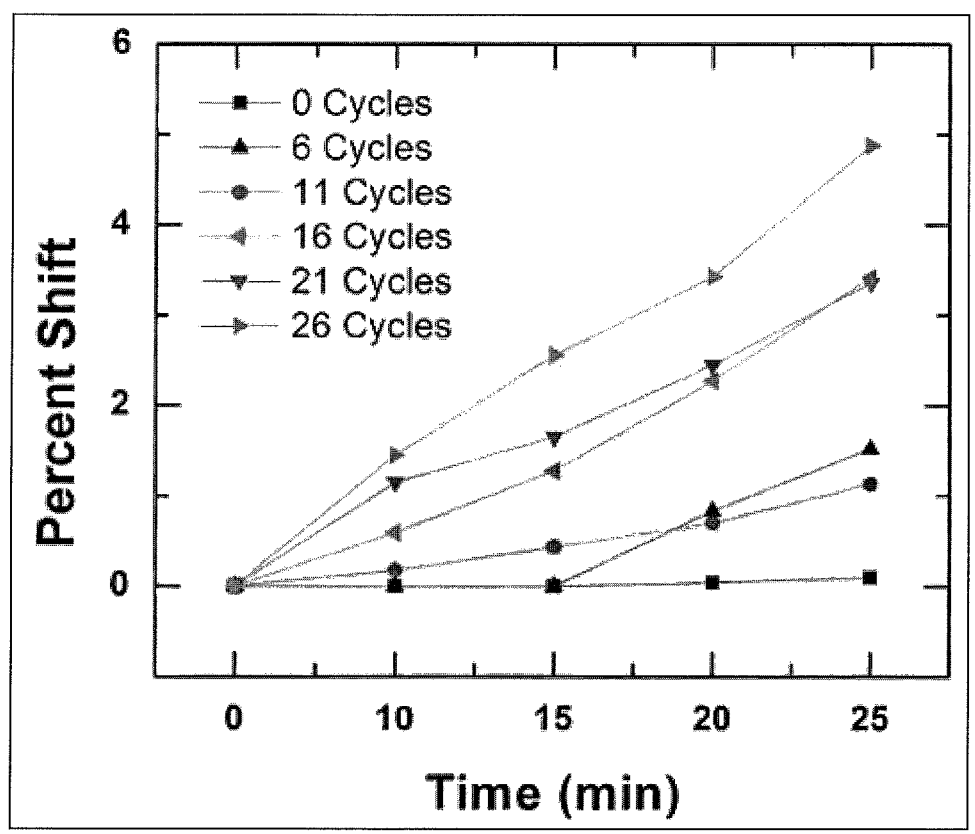
FIG. 18 depicts percent shift in the measured real component of the AC impedance (Z) as a function of PCR cycles and as a function of time The same reference numerals refer to the same parts throughout the various figures.

FIG. 18 depicts a quantitative curve of the percent shift in the measured real component of the AC impedance (Z') as a function of PCR cycles and as a function of time.

SUMMARY OF THE DISCLOSURE

The present microchamber electrochemical cell includes a substrate, opposing electrodes and at least one nanoslot. The substrate is configured to define a pair of opposing fluid reservoirs. The pair of opposing electrodes are respectively positioned within the opposing fluid reservoirs. Each nanoslot fluidly connects the opposing fluid reservoirs together. The opposing fluid reservoirs are fluidly connected to each other only through each nanoslot and each nanoslot is physical restricted to less than 500 nanometers. The methods include of using the microchamber electrochemical cell to perform quantitative analysis of various charged macromolecules. One method includes the steps of coupling, filling, measuring, obtaining, performing, and preparing.

The present disclosure allows real-time detection and quantification of DNA amplification without optical detection or fluorophore labeling. The microchamber electrochemical cell requires using only a miniature impedance meter. The small nanoslot of the microchamber electrochemical cell can be easily integrated with a portable PCR chip. The detection or measurements steps using the microchamber electrochemical cell can be implemented in parallel with the PCR cycles and hence can be programmed to terminate the PCR process whenever detection and quantification have been achieved. This new technology hence offers a rapid, portable, accurate, robust, and inexpensive real-time quantitative analysis of charged macromolecules such as those prepared in PCR synthesis designs.

The present disclosure is based on a fundamental observation—that PCR amplification converts small charged molecules into large DNA molecules (macro-ions) at an exponential rate and thus changes the conductivity of the PCR solution. Because of the high ionic strength of the PCR solution, the resulting conductance change is usually below the detection threshold. However, by combining new knowledge about electrokinetics in nanoslots and molecular dielectrophoresis, the new technology isolates the DNAs at an advantageous location to allow sensitive impedance detection.

Large DNA molecules have much larger dielectrophoretic mobility than the smaller molecules. As such, when the PCR solution is driven periodically in time by an AC electric field near an ion-selective nanoslot for which the DNA is a co-ion, the DNAs will be preferentially concentrated at a small region (10 microns to mm depending on the voltage) in front of the nanoslot entrance. The DNAs are driven to the nanoslot by dielectrophoretic forces towards the high-field region within the nanoslot. However, because the DNAs are co-ions of the nanoslot, they cannot enter the slot and are hence concentrated at the entrance. A depletion layer develops periodically at alternating entrances of the nanoslot every half cycle at a sufficiently high voltage and low frequency. The depletion layer is nearly ion-free except for the concentrated DNAs and their small counterions. Without the DNAs, a completely deionized depletion layer develops. Due to the high valency of the DNA macro-ions, their presence in the depletion layer introduces a surfeit of counterions that significantly increases the conductivity of the otherwise ion-free depletion layer. Because the depletion layer is the region with the lowest conductivity in the entire device, the presence of DNA molecules can sensitively change the nanoslot overall conductance. This DNA-mediated conductance change can be monitored with a low-frequency impedance spectrometry driven by a hand-held potentiostat. The impedance shift due to the presence of DNA has been measured to be as large as mega Ohms, thus allowing sensitive quantification of the number of DNAs. The entire nanoslot sensor can be integrated into a PCR chip to continuously monitor the amplification factor with a miniature impedance meter.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents.

What is claimed is:

1. A quantitative method for analyzing a macromolecule comprising:
   making an assay mixture containing the macromolecule;
   getting a microchamber electrochemical cell comprising:

a substrate defining a pair of opposing fluid reservoirs;
a pair of opposing electrodes in the opposing fluid reservoirs;
at least one nanoslot fluidly connecting together the opposing fluid reservoirs such that the opposing fluid reservoirs are fluidly connected to each other only through each nanoslot in which the height of each nanoslot is restricted to be less than the size of the macromolecule; and
an impedance measuring device;
flooding the opposing fluid reservoirs of the microchamber electrochemical cell with the assay mixture such that both opposing fluid reservoirs are in fluid communications with each other;
connecting the opposing electrodes to the impedance measuring device;
detecting an AC impedance between the opposing electrodes through each nanoslot while providing an AC sinusoidal electromagnetic perturbation; and
comparing the detected AC impedance to a control AC impedance to determine an impedance shift, wherein the impedance shift empirically correlates to a quantification of the number of macromolecules.

2. The method of claim 1, wherein the AC sinusoisal electromagnetic perturbance is at a frequency between 10 MHz to 0.01 Hz with an AC amplitude between 1 mV to 10 V.

3. The method of claim 1, wherein the height of each nanoslot is physically restricted to be no more than 500 nanometers.

4. The method of claim 1, further comprising correlating the AC impedance measured across the pair of opposing electrodes with a molar concentration of the macromolecule.

5. The method of claim 1, wherein the macromolecule is selected from the group consisting of a DNA macromolecule, an RNA macromolecule, a protein macromolecule, and an organic polymer macromolecule.

6. The method of claim 1, wherein the AC sinusoidal electromagnetic perturbation is at a single frequency of about 10 Hz.

7. The method of claim 1, wherein the frequency of the AC sinusoidal electromagnetic perturbation is frequency swept between about 1 MHz to 0.1 Hz and the AC impedance measured is an AC impedance spectrum.

8. The method of claim 1, wherein the measured AC impedance is a real component of the AC impedance (Z').

9. The method of claim 1, wherein the measured AC impedance is an AC impedance modulus (Z).

10. A microchamber electrochemical cell comprising:
a substrate defining a pair of opposing fluid reservoirs for receiving a solution of target macromolecules;
a pair of opposing electrodes in the opposing fluid reservoirs;
at least one nanoslot fluidly connecting together the opposing fluid reservoirs such that the opposing fluid reservoirs are fluidly connected to each other only through each nanoslot in which a maximum opening size of each nanoslot is restricted to be less than the size of the target macromolecule;
an impedance measuring device coupled to the opposing electrodes to measure the impedance between the electrodes; and
a processor adapted to analyze the measured impedance to determine the presence of the target macromolecule by comparing the measured impedance to a control impedance to determine an impedance shift, wherein the impedance shift empirically correlates to the presence of the target macromolecule.

11. The microchamber electrochemical cell of claim 10, further comprising a plurality of nanoslots.

12. The microchamber electrochemical cell of claim 10, wherein each nanoslot is composed of material selected from the group consisting of quartz, silica, silicon, polypropylene, polyethylene, polyethylene terephthalate, polyurethanes, polyacryls, polymethacryls, epoxy polymers, polystyrenes, polysiloxanes, and admixtures thereof.

13. The microchamber electrochemical cell of claim 10, wherein the impedance measuring device is configured to impose an AC sinusoidal electromagnetic perturbation and is configured to measure a resultant impedance modulus across the opposing electrodes through each nanoslot.

14. The microchamber electrochemical cell of claim 13, wherein the AC sinusoidal electromagnetic perturbation is at a single set frequency between 10 MHz to 0.01 Hz with an AC amplitude between 1 mV to 10 V.

15. The microchamber electrochemical cell of claim 13, wherein the impedance measuring device is configured to provide AC sinusoidal frequency perturbations swept between 10 MHz to 0.01 Hz having an AC amplitude of between 1 mV to 10 V and configured to measure real and imaginary components of a resultant impedance spectrum measured across the opposing electrodes through each nanoslot.

16. The microchamber electrochemical cell of claim 10, wherein the impedance measuring device is also configured to impose a DC voltage across the opposing electrodes.

17. The microchamber electrochemical cell of claim 10 further comprises a pair of opposing inlet/outlet ports through the substrate which are in fluid communications with the opposing reservoirs.

18. The microchamber electrochemical cell of claim 10, wherein the opposing electrodes are made of material selected from the group consisting of aluminum, carbon, chromium, cobalt, germanium, gold, graphite, graphene, iridium, molybdenum, osmium, palladium, platinum, ruthenium, rhodium, silicon, tantalum, titanium, titanium nitride, tungsten, tungsten nitride, vanadium, vitreous carbon, and mixtures thereof.

19. The microchamber electrochemical cell of claim 10, wherein the maximum opening size of each nanoslot is physically restricted to 500 nanometers or less.

20. The microchamber electrochemical cell of claim 19, wherein a minimum opening size of each nanoslot is at least 50 nanometers.

21. The microchamber electrochemical cell of claim 10, wherein the maximum opening size of each nanoslot is physically restricted to 200 nanometers.

22. The microchamber electrochemical cell of claim 10, wherein the substrate is made of material selected from the group consisting of quartz, silica, silicon, polypropylene, polyethylene, polyethylene terephthalate, polyurethanes, polyacryls, polymethacryls, epoxy polymers, polystyrenes, polysiloxanes, polyethyleneterephthalate, polystyrene, and admixtures thereof.

23. The microchamber electrochemical cell of claim 10, wherein the opposing fluid reservoirs comprise a total volume of between about 50 to 5000 microliters.

24. A real-time PCR (Polymerase Chain Reaction) quantitative method comprising:
preparing a PCR assay mixture comprising a target template, complementary primers, a buffer, a salt, a polymerase enzyme, and NTP (nucleotide triphosphate) monomers;

obtaining a microchamber electrochemical cell comprising:
- a substrate defining a pair of opposing fluid reservoirs;
- a pair of opposing electrodes in the opposing fluid reservoirs;
- at least one nanoslot fluidly connecting together the opposing fluid reservoirs such that the opposing fluid reservoirs are fluidly connected to each other only through each nanoslot in the height of each nanoslot is restricted to prevent the passage of the target template therethrough; and
- an impedance measuring device;

filling the opposing fluid reservoirs of the microchamber electrochemical cell with the PCR assay mixture such that both opposing fluid reservoirs are in fluid communication with each other through each nanoslot;

performing several PCR cycles in which each PCR cycle comprises a denaturation step, an annealing step and an elongation step to produce amplicons of the target template; coupling the opposing electrodes to the impedance measuring device;

measuring an AC impedance across the opposing electrodes while providing an AC sinusoidal electromagnetic perturbation; and comparing the detected AC impedance to a control AC impedance to determine an impedance shift, wherein the impedance shift empirically correlates to a quantification of the target within the PCR assay mixture.

25. The method of claim 24, wherein a maximum opening size of each nanoslot is 500 nanometers or less.

26. The method of claim 24, wherein the AC sinusoidal electromagnetic perturbation is at a frequency between 10 MHz to 0.01 Hz with an AC amplitude between 1 mV to 10 V.

27. The method of claim 24, further comprising correlating the AC impedance measured across the pair of opposing electrodes with a molar concentration of the amplicons.

28. The method of claim 24, wherein the AC impedance is measured at a temperature of about 20° C.

29. The method of claim 24, wherein the AC sinusoidal electromagnetic perturbation is at a single frequency of about 10 Hz.

30. The method of claim 24, wherein the AC sinusoidal electromagnetic perturbation is frequency swept between about 1 MHz to 0.1 Hz and the AC impedance measured is an impedance spectrum.

31. The method of claim 24, wherein the measured AC impedance is a real component of the AC impedance ($Z'$).

32. The method of claim 24, wherein the measured AC impedance is an AC impedance modulus ($Z$).

33. The method of claim 24, wherein the NTP monomers comprise deoxynucleotide triphosphates (dNTP) monomers or ribosenucleotide triphosphate (rNTP) monomers, the complementary primers are sense and antisense primers, the target template comprises a DNA target template or an RNA target template, the polymerase enzyme is Taq polymerase, the salt comprises magnesium divalent cations and potassium cations.

* * * * *